United States Patent
Venczel et al.

(10) Patent No.: US 11,590,206 B2
(45) Date of Patent: Feb. 28, 2023

(54) LIQUID PHARMACEUTICAL COMPOSITION

(71) Applicant: SANOFI, Paris (FR)

(72) Inventors: Marta Venczel, Frankfurt am Main (DE); Nino Meyer, Frankfurt am Main (DE); Walter Kamm, Frankfurt am Main (DE); Norbert Nagel, Frankfurt am Main (DE); Bruno Baumgartner, Frankfurt am Main (DE)

(73) Assignee: SANOFI, Paris (FR)

( * ) Notice: Subject to any disclaimer, the term of this patent is extended or adjusted under 35 U.S.C. 154(b) by 262 days.

(21) Appl. No.: 16/768,351

(22) PCT Filed: Dec. 20, 2018

(86) PCT No.: PCT/EP2018/086167
§ 371 (c)(1),
(2) Date: May 29, 2020

(87) PCT Pub. No.: WO2019/122109
PCT Pub. Date: Jun. 27, 2019

(65) Prior Publication Data
US 2022/0160837 A1 May 26, 2022

(30) Foreign Application Priority Data

Dec. 21, 2017 (EP) ..................... 17306875

(51) Int. Cl.
*A61K 38/26* (2006.01)
*A61K 47/02* (2006.01)
*A61K 47/10* (2017.01)

(52) U.S. Cl.
CPC .............. *A61K 38/26* (2013.01); *A61K 47/02* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 2012/0283170 A1* | 11/2012 | Lau | A61P 9/10 514/6.9 |
| 2019/0060410 A1* | 2/2019 | Liu | A61K 47/10 |

FOREIGN PATENT DOCUMENTS

| | | | | |
|---|---|---|---|---|
| WO | WO-2008082656 A1 * | 7/2008 | ............. | A61K 31/70 |
| WO | WO 2011/058082 A1 | 5/2011 | | |
| WO | WO 2014/056872 A1 | 4/2014 | | |
| WO | WO-2014056872 A1 * | 4/2014 | ......... | A61K 38/2264 |
| WO | WO-2016180353 A1 * | 11/2016 | ............. | A61K 38/26 |

OTHER PUBLICATIONS

Buse et al. ("Effects of Exenatide (Exendin-4) on Glycemic Control Over 30 Weeks in Sulfonylurea-Treated Patients With Type 2 Diabetes," Diabetes Care, 2004, vol. 27, pp. 2628-2635) (Year: 2004).*
EMA Summary of product characteristics Saxenda®, p. 16, retrieved on Dec. 19, 2017.
EMA Summary of product characteristics Victoza®, p. 15, retrieved on Dec. 19, 2017.
FDA reference ID: 3677762, section "Injection site reactions", p. 10, retrieved on Dec. 19, 2017.
Heljo et al. "Interactions Between Peptide and Preservatives: Effects on Peptide Self-Interactions and Antimicrobial Efficiency In Aqueous Multi-Dose Formulations", Pharmaceutical Research, Apr. 17, 2015, vol. 32, Issue 10, pp. 3201-3212.
International Search Report and Written Opinion in PCT International Patent Application No. PCT/EP2018/086167, dated Mar. 15, 2019.
Novo Nordisk Australia: "Australian Product Information for Saxenda® Liraglutide solution for injection", Australian Register of Therapeutic Goods (ARTG), retrieved on Dec. 19, 2017.
Novo Nordisk Australia: "Australian Product Information for Victoza® Liraglutide", Australian Register of Therapeutic Goods (ARTG), retrieved on Dec. 19, 2017.
Rote Liste 2016, 12 034 (Novo Nordisk), "Victoza®6 mg/ml Injektionslösung in einem Fertigpen", pp. 402-403.
Wang et al. "Quantitative Evaluation of Colloidal Stability of Antibody Solutions using PEG-Induced Liquid-Liquid Phase Separation", Molecular Pharmaceutics, 2014, vol. 11, No. 5, pp. 1391-1402.

* cited by examiner

*Primary Examiner* — Christina Bradley
(74) *Attorney, Agent, or Firm* — Lathrop GPM LLP; James H. Velema, Esq.

(57) ABSTRACT

The present invention relates to a liquid pharmaceutical composition comprising a peptide of SEQ ID NO.: 2 as an active pharmaceutical ingredient. The composition of the present invention is suitable for medical use in humans, for example in the treatment of disorders of a metabolic syndrome or diabetes or obesity or for reduction of excess food intake.

Figure 1:
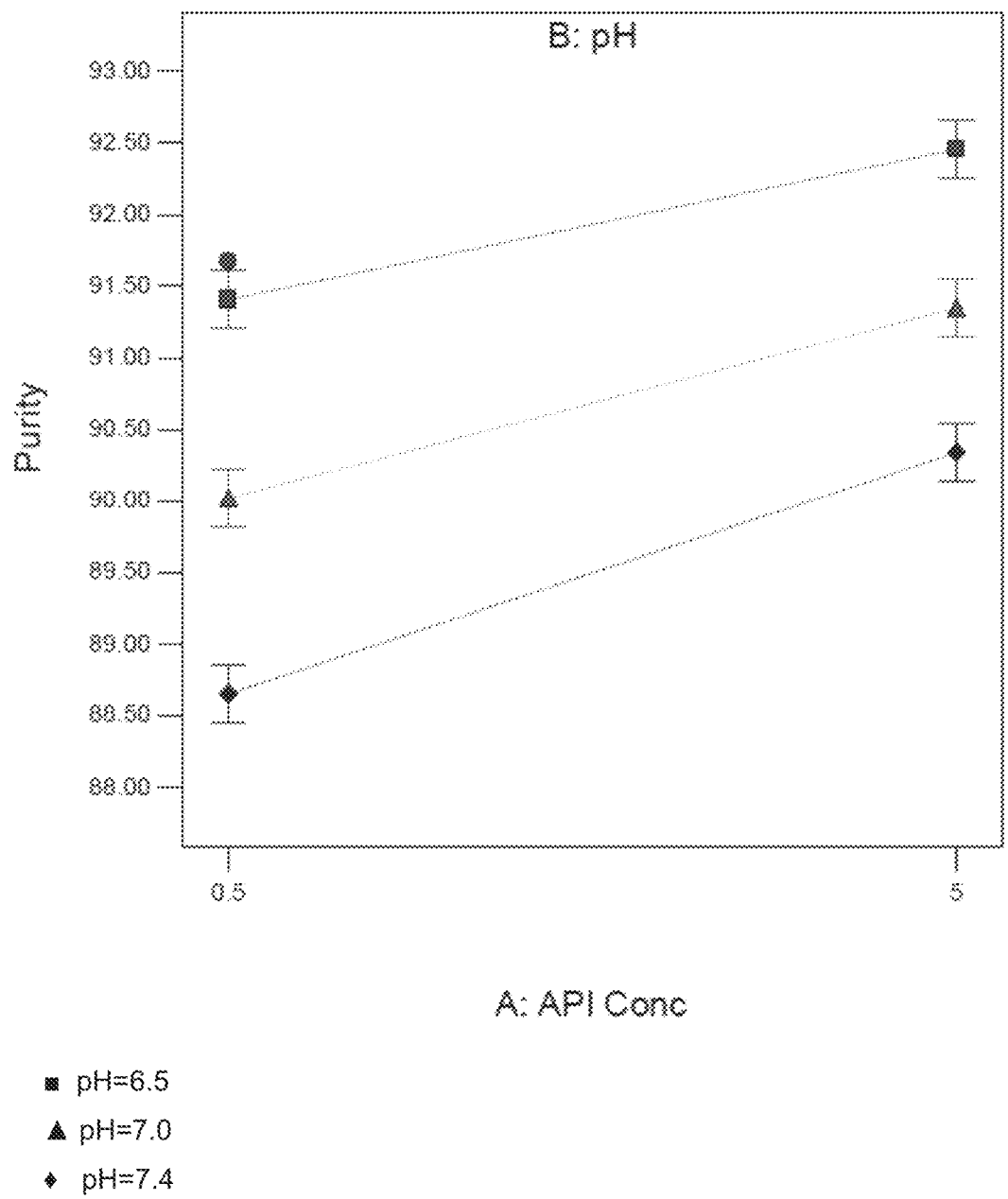

16 Claims, 8 Drawing Sheets
Specification includes a Sequence Listing.

LIQUID PHARMACEUTICAL COMPOSITION

RELATED APPLICATIONS

This application is a 35 U.S.C. § 371 filing of International Patent Application No. PCT/EP2018/086167, filed Dec. 20, 2018, which claims priority to European Patent Application No. 17306875.0, filed Dec. 21, 2017, the entire disclosures of which are hereby incorporated herein by reference.

FIELD OF THE INVENTION

The present invention relates to a liquid pharmaceutical composition comprising a peptide of SEQ ID NO.: 2 as an active pharmaceutical ingredient. The composition of the present invention is suitable for medical use in humans, for example in the treatment of disorders of a metabolic syndrome or diabetes or obesity or for reduction of excess food intake.

BACKGROUND OF THE INVENTION

WO 2014/056872 A1, the content of which is incorporated by reference herein discloses the peptide of SEQ ID NO.: 2:

```
                              (SEQ ID NO.: 2)
 1         5         10
H-dSer-Q-G-T-F-T-S-D-L-S-K-Q-K(γE-x53)

15        20
-E-S-K-A-A-Q-D-F-I-E-

25        30        35
W-L-K-A-G-G-P-S-S-G-A-P-P-P-S-NH₂
``` wherein γE-x53 is (S)-4-Carboxy-4-hexadecanoylamino-butyryl- as shown below:

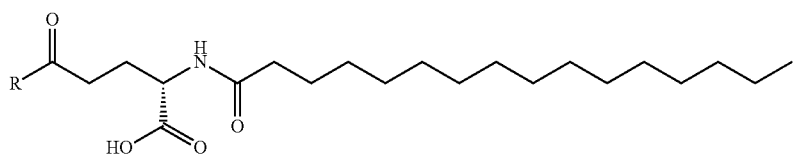

which activates the glucagon-like peptide-1 (GLP-1) receptor and the glucagon receptor. General remarks for a formulation are given, but no data regarding long term stability of specific formulations.

Liraglutide and a pharmaceutical composition thereof are publicly known. It is a marketed chemically modified analogue of GLP-1 in which, among other modifications, a fatty acid is linked to a lysine in position 20 leading to a prolonged duration of action.

The amino acid sequence of Liraglutide is shown as SEQ ID NO.: 1:

```
(SEQ ID NO.: 1)
 1         5         10        15        20
H-A-E-G-T-F-T-S-D-V-S-S-Y-L-E-G-Q-A-A-K ((S)-4-Carboxy-4-hexadecanoylamino-butyryl-)-

25        30
E-F-I-A-W-L-V-R-G-R-G-OH
```

The marketed formulation of liraglutide comprises the active agent liraglutide, sodium monohydrogen phosphate dihydrate, propylene glycol, phenol, and water for injection at pH 8.15 (see Novo Nordisk Australia: "*Product Information Liraglutide Victoza®*" and Novo Nordisk Australia: "*Product Information Liraglutide Saxenda®*, available online via the publicly accessible version of the Australian Register of Therapeutic Goods (ARTG; retrieved on 19 Dec. 2017 under URL https://www.ebs.tga.gov.au/ebs/picmi/picmirepository.nsf/PICMI?OpenForm&t=&q=victoza&r=https://www.ebs.tga.gov.au/ (for Victoza) and https://www.tga.gov.au/artg/artg-id-225804 (for Saxenda); Rote Liste 2016, page 402). Two formulations by Novo Nordisk, Victoza® and Saxenda®, are mentioned in the "Rote Liste": Victoza® 6 mg/mL solution for injection in a pen device, (access code Rote Liste: ATC: A10BX07) and Saxenda® 6 mg/mL solution for injection in a pen device (access code Rote Liste: ATC: A10BX07). Both formulations comprise the active agent liraglutide, sodium monohydrogen phosphate dihydrate, propylene glycol, phenol, and water for injection.

These formulations have certain disadvantages due to the presence of propylene glycol, e.g. because parenteral administration may cause pain or irritation. Further, from the viewpoint of patient tolerability, the alkaline pH (pH>8) is disadvantageous, taking into consideration that the formulation has to be injected daily (see FDA reference ID: 3677762, retrieved on 19 Dec. 2017 under URL http://www.accessdata.fda.gov/drugsatfda_docs/label/2014/206321Orig1s000lbl.pdf; page 10, section "*Injection site reactions*"). There, it is described that the most common injection site reactions, each reported by 1% to 2.5% of Saxenda-treated patients and more commonly than by placebo-treated patients, included erythema, pruritus, and rash at the injection site.

BRIEF SUMMARY OF THE INVENTION

It was an object of the present invention to provide a stable liquid composition comprising the peptide of SEQ ID NO.: 2 or a pharmaceutically acceptable salt thereof. This object was achieved by formulating the peptide of SEQ ID NO.: 2 (or a pharmaceutically acceptable salt thereof) with sodium chloride as an excipient. In some instances, the composition according to the invention is also referred to herein as "formulation".

It was found that, surprisingly, the addition of sodium chloride is able to improve the storage stability of a composition according to the present invention comprising the peptide of SEQ ID NO.: 2. Sodium chloride increases the physical stability of the compositions of the invention and decreases the adsorption of the active pharmaceutical ingredient to the wall of the primary containers.

Further, it was surprisingly found that sodium chloride improves the storage stability of the compositions also by reducing the formation of proteins of high molecular weight and the total impurities. These parameters are, individually or together, a measure of the chemical integrity of the compositions.

Accordingly, the present invention provides a liquid composition comprising a peptide of SEQ ID NO.: 2 and/or a pharmaceutically acceptable salt thereof, sodium chloride, and a liquid carrier. Further, the present invention provides a liquid composition comprising a peptide of SEQ ID NO.: 2 and/or a pharmaceutically acceptable salt thereof as an active pharmaceutical ingredient, sodium chloride as an excipient, and a liquid carrier.

In one embodiment, the composition of the invention is stable at a physiological pH or a slightly acidic pH. In some embodiments, the composition of the invention is stable at a pH of about 6 to about 7, optionally in the presence of a pharmaceutically acceptable preservative, such as m-cresol, and in the absence of organic solvents, such as glycerol and propylene glycol. Stability in the absence of organic solvents, e.g. in the absence of propylene glycol, is surprising in view of the hydrophobic and lipophilic moiety attached to the side chain of lysine at position 14 of SEQ ID NO.: 2.

In comparison, the marketed formulation of liraglutide (Novo Nordisk Victoza®, Saxenda®) has an alkaline pH and contains propylene glycol (see EMA Summary of product characteristics Victoza®, retrieved on 19 Dec. 2017 under URL http://www.ema.europa.eu/docs/en_GB/document_library/EPAR_-_Product_Information/human/001026/WC500050017.pdf (page 15) and EMA Summary of product characteristics Saxenda®, retrieved on 19 Dec. 2017 under URL http://www.ema.europa.eu/docs/en_GB/document_library/EPAR_-_Product_Information/human/003780/WC500185786.pdf (page 16)).

Furthermore, a formulation of SEQ ID NO.: 2 with m-cresol as a microbiological preservative was found. m-Cresol has a higher binding property to the surface of peptides than phenol. The formulation of liraglutide contains phenol as a microbiological preservative (Novo Nordisk Victoza®, Saxenda®; see e.g. Interactions Between Peptide and Preservatives: Effects on Peptide Self-Interactions and Antimicrobial Efficiency In Aqueous Multi-Dose Formulations, Pharmaceutical Research, October 2015, Volume 32, Issue 10, pp 3201-3212).

In addition, it was found that the absence of organic solvents from the liquid carrier of the composition is advantageous. Accordingly, in certain embodiments, the liquid carrier of the composition of the invention is free of any organic solvent, particularly free of glycerol and/or propylene glycol. Further, it was found that the absence of tonicity adjusters (other than sodium chloride) is advantageous. Accordingly, in certain embodiments, the composition of the invention is free of tonicity adjusters other than sodium chloride, such as mannitol.

Further, it was surprisingly found that the composition according to the invention can e.g. be prepared with an aqueous liquid carrier in the absence of surfactants, despite the presence of a lipophilic moiety attached to the ε-$NH_2$ group of a lysine residue in the peptide of SEQ ID NO.: 2. Accordingly, in certain embodiments, the composition of the invention is free of surfactants, particularly polysorbates and/or poloxamers.

Thus, the liquid composition described herein was found to have sufficient stability, i.e. biological activity, chemical integrity and/or physical integrity after storage, to provide a shelf life (i.e. period of time during which the composition may be stored without deteriorating and remains suitable for use), particularly in a closed container, of at least one month, particularly at least three months, more particularly at least six months, at a temperature of +5° C., +25° C. or +37° C. In certain embodiments, the liquid composition comprises a peptide of SEQ ID NO.: 2, sodium chloride and m-cresol, but is free of both organic solvents and surfactants. The compatibility of these different compounds, resulting in high biological activity, chemical integrity and/or physical integrity was surprising.

In another aspect, the invention relates to a medical use of the claimed composition. Medical indications of interest are for example disorders of a metabolic syndrome or diabetes or obesity or a use for the reduction of excess food intake. In specific embodiments, the claimed composition is for use in a method of treating diabetes mellitus, e.g. type II diabetes mellitus, and/or for use in a method of treating obesity.

DETAILED DESCRIPTION OF THE INVENTION

The composition of the present invention comprises a peptide of SEQ ID NO.: 2 and/or a pharmaceutically acceptable salt thereof as an active pharmaceutical ingredient.

The term "pharmaceutically acceptable salts" means salts of the compounds of the invention which are safe and effective for use in humans. Pharmaceutically acceptable salts may include, but are not limited to, acid addition salts and basic salts.

As mentioned above, the invention provides a liquid composition comprising a peptide of SEQ ID NO.: 2 and/or a pharmaceutically acceptable salt thereof, sodium chloride, and a liquid carrier. Further, the invention provides a liquid composition comprising a peptide of SEQ ID NO.: 2 and/or a pharmaceutically acceptable salt thereof as an active pharmaceutical ingredient, sodium chloride as an excipient, and a liquid carrier.

In one embodiment of the composition of the invention, the active pharmaceutical ingredient may be present in an amount of about 1 µg/ml to about 75 mg/ml, e.g. in an amount of about 1 µg/ml to about 10 mg/ml based on the weight of the peptide of SEQ ID NO.: 2. In a further embodiment, the active pharmaceutical ingredient may be present in an amount of 1 µg/ml to 75 mg/ml, e.g. in an amount of 1 µg/ml to 10 mg/ml based on the weight of the peptide of SEQ ID NO.: 2. In another embodiment, the active pharmaceutical ingredient is present in an amount of 0.5 mg/ml to 5 mg/ml.

It has been found that sodium chloride increases storage stability of the composition in contrast to other tonicity adjusters such as mannitol and/or glycerol. In particular embodiments, sodium chloride is present in an amount of about 0.5 mg/ml to about 9 mg/ml, more particularly in an amount of about 5 mg/ml to about 9 mg/ml, and even more particularly in an amount of 6.0 mg/ml to about 6.5 mg/ml such as 6.30 mg/ml.

The composition may further comprise a pharmaceutically acceptable preservative, for example, phenol and/or m-cresol, particularly m-cresol. The amount of m-cresol is typically from about 2 mg/ml to about 5 mg/ml, particularly from about 3.0 mg/ml to about 3.5 mg/ml, such as 3.15 mg/ml.

The composition according to the present invention may further comprise a pharmaceutically acceptable buffer. Particularly, the pharmaceutically acceptable buffer is selected from the group consisting of a phosphate buffer, a citrate buffer, and a phosphate-citrate buffer in different hydrate and/or solvate forms such as an anhydrate, monohydrate, dihydrate, heptahydrate, octahydrate and dodecahydrate.

In certain embodiments, the composition comprises a phosphate buffer, particularly a sodium phosphate buffer. The phosphate buffer may be made in situ by mixing phosphoric acid and sodium hydroxide, or it may be composed of a dihydrogen phosphate salt and a monohydrogen phosphate salt, e.g. sodium dihydrogen phosphate dihydrate and disodium hydrogen phosphate dodecahydrate. The phosphate buffer, possibly together with any other phosphate salt, is typically present in a concentration of about 5 mM to 100 mM, e.g. 5 mM to 100 mM, such as 30 mM. The phosphate buffer typically has a pH of from 5.8 to 8.0, such as 6.0 to 7.4.

If present, the composition may comprise the buffer materials, e.g. sodium dihydrogen phosphate dihydrate and disodium hydrogen phosphate dodecahydrate, in different molar ratios ranging from about 5:1 to 1:5, or from about 2:1 to 1:2, depending on the desired pH value of the composition.

For example, the molar ratio of the buffer materials when using a phosphate buffer, e.g. a two-component phosphate buffer such as sodium dihydrogen phosphate dihydrate and disodium hydrogen phosphate dodecahydrate, may be about 5:3, 5:2, 5:1, 1:5, 2:5, or 3:5, particularly about 2:1 or about 1:2 or about 1:1. In one embodiment, the molar ratio of sodium dihydrogen phosphate dihydrate and disodium hydrogen phosphate dodecahydrate may be 5:3, 5:2, 5:1, 1:5, 2:5, or 3:5, particularly 2:1 or 1:2. In another embodiment, the molar ratio of sodium dihydrogen phosphate dihydrate and disodium hydrogen phosphate dodecahydrate may be 1:1.8.

In other embodiments, the composition comprises a sodium citrate buffer. The citrate buffer may be made in situ by mixing citric acid and sodium hydroxide, or it may be composed of a citric acid monohydrate and a trisodium citrate, e.g. trisodium citrate anhydrate or dihydrate. The citrate buffer is typically present in a concentration of about 5 mM to 100 mM, e.g. 5 mM to 100 mM, such as 30 mM. The citrate buffer typically has a pH of from 3.0 to 7.0, such as 4.5 to 6.6.

If present, the composition may comprise the buffer materials, e.g. citric acid and trisodium citrate, in different molar ratios ranging from about 5:1 to 1:5, or 2:1 to 1:2, depending on the desired pH value of the composition.

In other preferred embodiments, the composition comprises a phosphate-citrate buffer. The phosphate-citrate buffer may be made by mixing citric acid and disodium hydrogen phosphate, or it may be composed of a citric acid anhydrate or monohydrate and disodium hydrogen phosphate anhydrate, dihydrate, heptahydrate, octahydrate or dodecahydrate. The phosphate-citrate buffer is typically present in a concentration of about 5 mM to 100 mM, e.g. 5 mM to 100 mM, such as 30 mM. The citrate buffer typically has a pH of from 3.0 to 7.0, such as 4.5 to 6.6.

If present, the composition may comprise the buffer materials, e.g. citric acid and disodium hydrogen phosphate, in different molar ratios ranging from about 5:1 to 1:5, or 2:1 to 1:2, depending on the desired pH value of the composition.

The composition of the present invention preferably has a physiological to slightly acidic pH, preferably a pH from about 6.0 to about 7.0, particularly from about 6.2 to about 6.9 such as about pH 6.6. The pH may be adjusted by appropriate selection of a buffer pH adjustment using a pharmaceutically acceptable acid such as hydrochloric acid (HCl) and/or a base such as sodium hydroxide (NaOH).

The composition of the invention comprises a liquid carrier. Typically, the liquid carrier is an aqueous liquid, particularly water. Usually the liquid carrier is substantially free of organic solvents. In the context of the present invention, the term "organic solvent" refers to a class of compounds commonly used in the pharmaceutical industry to dissolve pharmaceutical ingredients. They usually have low molecular weight, are lipophilic and volatile, and are liquid at room temperature. They comprise both aliphatic compounds and aromatic compounds. As an example, alcohols such as ethanol, glycerol, propylene glycol etc. may be mentioned. Propylene glycol is defined as an organic solvent in the context of the present invention, though it is sometimes used as a tonicity adjuster in the art.

In the context of the present invention, the term "substantially free of" means that a respective composition contains less than 5% (w/w), less than 2.5% (w/w) or less than 1% (w/w) of a given compound. A "compound" in the context of the invention is any chemical substance composed of identical molecules consisting of atoms of two or more chemical elements. For example, when the given compound is propylene glycol, a composition substantially free of propylene glycol will contain less than 5% (w/w), less than 2.5% (w/w) or less than 1% (w/w) propylene glycol.

More particularly, the liquid carrier is free of organic solvents such as glycerol and propylene glycol. In the context of the present invention, the term "free of" means that a respective composition contains less than 0.01% (w/w), particularly less than 0.001% (w/w) of a given compound. It is intended that, when the liquid carrier is free of organic solvents, the whole liquid composition is free of organic solvents.

In particular embodiments, the composition of the present invention is substantially free or free of surfactants such as a polyhydric alcohol or esters and ethers thereof. The composition according to the present invention is more particularly free of fatty acid esters and ethers of glycerol and sorbitol such as Span®, Tween®, Myrj®, Brij®, Cremophor®.

Furthermore, the compositions according to the present invention particularly are free of polyols selected from the group consisting of polypropylene glycols, polyethylene glycols, polysorbates, poloxamers, Pluronics, and Tetronics. More particularly, the composition according to the present invention is free of polysorbates, and/or poloxamers.

More particularly, the composition according to the present invention is substantially free, preferably free, of polysorbates, such as, for example, polysorbate 20 and/or polysorbate 80.

More particularly, the composition according to the present invention is substantially free, preferably free, of poloxamers, such as, for example, poloxamer 188.

In certain embodiments, the composition is free of both polysorbates and poloxamers.

Furthermore, the composition of the invention may be free of tonicity adjusters different from sodium chloride. The term "tonicity adjuster" or "tonicity agent" within the present invention refers to compounds that can render liquid compositions isotonic with respect to certain membranes (e.g. of blood cells or of cardiovascular tissue), such that e.g. damage to blood cells or cardiovascular tissue can be prevented, when the composition is applied intravenously. For example, the composition is, in certain embodiments, substantially free or free of glycerol, dextrose, lactose, sorbitol and mannitol. Particularly, the composition is free of mannitol.

In certain embodiments, the composition is substantially free or free of both mannitol and propylene glycol (discussed above under "organic solvents").

The composition of the invention is physically and chemically stable for at least 2 years with and without addition of surfactants, e.g. poloxamers, and/or tonicity adjusters such as mannitol, and/or organic solvents such as propylene glycol.

According to the present invention, a composition is provided which exhibits biological, chemical, and/or physical integrity of the active agent (active pharmaceutical ingredient(s) or API(s)), i.e. a peptide of SEQ ID NO.: 2, a pharmaceutically acceptable salt of SEQ ID NO.: 2, or a combination of a peptide of SEQ ID NO.: 2 and at least one pharmaceutically acceptable salt thereof after storage, e.g. after storage for one month, three months, six months, nine months, twelve months or twenty-four months at a temperature of +5° C. or after storage for one month, three months, or six months at a temperature of +25° C.

In the present application, the term "biological activity" means the activity of the peptide of SEQ ID NO.: 2, which is used in the composition according to the present invention. Methods for determining the activity of a GLP-1 receptor agonist are known to a person skilled in the art.

More particularly, the composition according to the present invention has, after storage for 1 month, 3 months, 6 months, 9 months, 12 months, 18 months or 24 months at a temperature of +5° C. or +25° C., a biological activity of at least 80%, at least 90%, at least 95%, or at least 98% of the activity at the start of storage.

In particular, the composition according to the present invention has a biological activity of GLP-1 and glucagon receptor agonists of at least 80% or at least 90% after storage for 12 months at +5° C., particularly for 24 months at +5° C.

More particularly, the composition according to the present invention exhibits chemical integrity after storage for 1 month, 3 months, 6 months, 9 months, 12 months, 18 months or 24 months. In the context of the present disclosure, chemical integrity is sometimes also referred to as chemical stability. Chemical integrity means, more particularly, that after storage at a temperature of +5° C., +25° C., or +37° C. the composition comprises at least 80%, at least 90%, at least 95%, or at least 98% of the active substance (API(s)), compared with the start of storage, in a substantially chemically unchanged form.

Chemical integrity can mean a very low proportion of proteins of high molecular weight in the composition according to the present invention. The proportion of proteins of high molecular weight with respect to the entire mass of the peptide of SEQ ID NO.: 2 present in the composition after storage for 18 months at +5° C., for 6 months at +25° C. and/or for 1 month at +37° C. is preferably below 2 wt-%. The amount of proteins of high molecular weight can, e.g., be determined using high performance size exclusion chromatography (HPSEC).

More particularly, the composition according to the present invention exhibits physical integrity after storage for 1 month, 3 months, 6 months, 9 months, 12 months, 18 months or 24 months. In the context of the present disclosure, physical integrity is sometimes also referred to as physical stability. Physical integrity means, more particularly, that after storage at a temperature of +5° C., +25° C., or +37° C., the composition comprises at least 80%, at least 90%, at least 95%, or at least 98% of the active substance, compared with the start of storage, in a substantially physically unchanged form.

Physical integrity can mean that the peptide of SEQ ID NO.: 2 does not form aggregates, such as, for example, fibrils. In some aspects, the pharmaceutical composition is free of aggregates, in particular aspects free of undesired larger covalent aggregates.

Oligomers are known to exist as covalent oligomers, which are also named high molecular weight proteins and which are typically undesired, and non-covalent oligomers linked to the quaternary structure of a peptide.

High molecular weight proteins are typically dimers or trimers of the peptide, which may for example form via intermolecular transamidation reactions following the formation of a cyclic anhydride intermediate or by other mechanisms.

Protein aggregates are typically large assemblies of many misfolded proteins, which are clumped together. Unfolding or misfolding of proteins may occur, if the protein in solution is exposed to stress such as heat, mechanical stress or hydrophobic surfaces. The assumed formation mechanism of aggregates is that the exposed hydrophobic portions of the protein interact with and attach to the exposed hydrophobic patches of other proteins. The most prominent representatives of protein aggregates are amyloid fibrils, which have a structured core, but also amorphous aggregates are known.

Within the context of this application, non-covalent oligomers linked to the quaternary structure of a peptide are not considered "aggregates" or "proteins of high molecular weight". Non-covalent oligomers can be characterized e.g. by small angle X-ray scattering (SAXS) which provides information on oligomer size and shape. The presence or absence of aggregates can be determined e.g. by Dynamic Light Scattering (DLS) to monitor the hydrodynamic diameter.

In solution under formulation conditions as specified herein, SEQ ID NO.: 2 can e.g. form a quaternary structure via non-covalent bonds. This is a reversible effect that is common and well known for proteins. For example also liraglutide and most marketed insulins are known to exist as physically bound oligomers in their respective solution formulations.

On the other hand, consistently low levels of covalently bound oligomers (high molecular weight proteins) were shown in stability studies (see Examples).

Small angle X-ray scattering (SAXS) investigations performed at a synchrotron light source (DESY Hamburg) can provide information on oligomer size and shape. The best fit between the experimentally observed small angle X-ray scattering curve and the calculated one can be obtained using a model in which SEQ ID NO.:2 is all hexameric in the formulations. All hexameric means that all peptide molecules are arranged in physical oligomers containing 6 molecules of SEQ ID NO.: 2. In addition, supplementary investigations by dynamic light scattering were performed with the drug product to monitor the hydrodynamic diameter of about 6 nanometers.

In summary, the investigations show the absence of undesired larger covalent aggregates in the drug substance (API(s)) and exemplary formulations according to the present invention. Low levels of high molecular weight proteins are considered as a quality attribute, which is routinely controlled.

In some embodiments, the composition of the invention comprises (a) a peptide of SEQ ID NO.:2 and/or a pharmaceutically acceptable salt thereof, (b) a sodium phosphate buffer of pH 6.0 to 6.9, a citrate buffer of pH 4.5 to 6.6, or a phosphate-citrate buffer of pH 4.5 to 6.6, particularly a sodium phosphate buffer of about pH 6.5 to 6.7, (c) m-cresol, (d) sodium chloride, and (e) water.

In some embodiments, the composition of the invention consists essentially of (a) a peptide of SEQ ID NO.:2 and/or a pharmaceutically acceptable salt thereof, (b) a sodium phosphate buffer of pH 6.0 to 6.9, a citrate buffer of pH 4.5 to 6.6, or a phosphate-citrate buffer of pH 4.5 to 6.6, particularly a sodium phosphate buffer of about pH 6.5 to 6.7, (c) m-cresol, (d) sodium chloride, and (e) water.

By "consisting essentially of" it is meant to include any elements listed after the phrase, and is limited to include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In specific embodiments, the composition of the invention consists of (a) a peptide of SEQ ID NO.:2 and/or a pharmaceutically acceptable salt thereof, (b) a sodium phosphate buffer of pH 6.0 to 6.9, particularly a sodium phosphate buffer of about pH 6.5 to 6.7, (c) m-cresol, (d) sodium chloride, and (e) water.

In certain preferred embodiments of the invention, the composition of the invention consists of (a) a peptide of SEQ ID NO.:2 and/or a pharmaceutically acceptable salt thereof, (b) a sodium phosphate buffer of pH 6.2 to 6.9, particularly a sodium phosphate buffer of about pH 6.5 to 6.7, (c) m-cresol, (d) sodium chloride, and (e) water.

In certain preferred embodiments, the composition of the present invention consists of (a) a peptide of SEQ ID NO.:2 and/or a pharmaceutically acceptable salt thereof in an amount of 0.5 mg/ml to 5 mg/ml, (b) $NaH_2PO_4 \times 2H_2O$ in an amount of 3.03 mg/ml and $Na_2HPO_4 \times 12H_2O$ in an amount of 3.77 mg/ml, (c) m-cresol in an amount of 3.15 mg/ml, (d) sodium chloride in an amount of 6.30 mg/ml, (e) optionally NaOH and/or HCl at pH 6.6, and (f) water, particularly water for injection.

In the present application, "about" means that the constituents can be present, for example, within the ranges of ±5%, ±10%, or ±20%, particularly ±5%, around the specified values in the compositions according to the present invention.

The composition of the present invention may comprise the peptide of SEQ ID NO.: 2 or a pharmaceutically acceptable salt thereof as the only active ingredient.

In certain embodiments, the liquid composition as claimed herein exhibits biological activity, chemical integrity, and physical integrity of the active ingredient(s) after storage.

The liquid composition of the present invention can be prepared for use in suitable pharmaceutical applications. Suitable pharmaceutical compositions may be in the form of one or more administration units.

Each of the above-mentioned administration units of the pharmaceutical composition of the invention may be provided in a package for easy transport and storage. The administration units are packaged in standard single or multi-dosage packaging, their form, material and shape depending on the type of units prepared. Liquid formulations can be packaged in single units, such as e.g. vials, cartridges, syringes/prefilled syringes, infusion bags, collapsible plastic bags, infusion bottles, blow-filled seal bottles or infusion tubings or in single or multiple dose injectable form, for example in the form of a pen device, pump or syringe and the single packaged units can be packaged in multi-pack containers. A single package may comprise only one or a plurality of administration units. The package may for example be made of paper, cardboard, paperboard, plastic, metal, combinations or laminates of one or more of paper, plastics and metal, or glass. Exemplary embodiments are glass or plastic bottles containing e.g. a solution, or vials, cartridges, syringes, infusion bags, infusion bottles, infusion tubings or ampoules containing a solution or suspension.

In certain embodiments administration units may be provided together with a device for application, for example together with a syringe, an injection pen or an autoinjector. Such devices may be provided separate from a pharmaceutical composition or prefilled with the pharmaceutical composition.

A "pen-type injection device", often briefly referred to as "injection pen", is typically an injection device having an elongated shape that resembles to a fountain pen for writing. Although such pens usually have a tubular cross-section, they could easily have a different cross-section such as triangular, rectangular or square or any variation around these geometries. Generally, pen-type injection devices comprise three primary elements: a cartridge section that includes a cartridge often contained within a housing or holder; a needle assembly connected to one end of the cartridge section; and a dosing section connected to the other end of the cartridge section. The cartridge, often also referred to as "ampoule", typically includes a reservoir that is filled with a medication, a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The administration of the administration units can take place once daily, twice daily, thrice daily, four times daily, five times daily, six times daily, seven times daily, or eight times daily. Any other daily administration of the administration unit is also presently encompassed.

The composition of the present invention is suitable for use in medicine, particularly for use in human medicine. Particularly, the composition is for injection, e.g. for subcutaneous, intramuscular, pulmonal, nasal, intrathecal or intravenous injection. In one embodiment, the composition is for subcutaneous and/or intravenous injection, in another embodiment for subcutaneous injection.

Further, the present invention relates to a method of treating a disorder comprising administering a therapeutically effective amount of a composition as described above to a patient in need thereof. Particularly, the patient is a human patient. The disorder may be diabetes mellitus, such as type I or type II diabetes mellitus, and/or obesity.

The term "therapeutically effective amount" refers to a non-toxic but sufficient amount of the active ingredient(s) (also referred to herein as active pharmaceutical ingredient (API)) to provide the desired therapeutic effect. For example, a "therapeutically effective amount" of a peptide of SEQ ID NO.: 2 is about 0.01 to about 50 mg/dose, particularly about 0.1 mg/dose to about 10 mg/dose. According to the present invention, the peptide of SEQ ID NO.: 2 may be administered alone, i.e. the peptide is administered as such or, preferably, in a formulation in which it is the sole active pharmaceutical ingredient.

The composition according to the present invention is intended particularly for treating diabetes mellitus and/or obesity, more particularly for treating type I or type II diabetes mellitus and/or for treating obesity. In certain embodiments, the composition is for use in a method of treating diabetes mellitus, particularly type II diabetes mellitus, and/or for use in a method of treating obesity. The composition according to the present invention may be used to control the fasting, postprandial, or/and postabsorptive plasma glucose concentration, to improve glucose tolerance, to prevent hypoglycemia, to prevent functional loss of the β-cells of the pancreas, to effect weight loss, or/and to prevent weight gain. Further possible indications are obesity and obesity in the presence of at least one weight-related comorbid condition, e.g. hypertension, type II diabetes mellitus and/or dyslipidemia.

The present invention further provides for the use of a composition according to the present invention in the manufacture of a pharmaceutical for treating diabetes mellitus and/or obesity, more particularly type I or type II diabetes mellitus and/or obesity. Patients treated can have an HbA1c value in the range of 7% to 10%.

The present invention further provides a method for manufacturing a composition according to the present invention, comprising formulating a peptide of SEQ ID NO.: 2 or/and a pharmaceutically acceptable salt thereof with sodium chloride and, optionally, at least one pharmaceutically acceptable excipient.

The present invention further provides for the use of the composition according to the invention in patients with type II diabetes mellitus as a supplement to a diet in order to improve blood sugar control with a once daily injection (e.g. reduces substantially and sustainably (>2 years) glucose (Δ HbA1c>−1.0%) and weight (>−10%)).

The invention is further elucidated by the following examples and figures.

LEGENDS TO THE FIGURES

FIG. 1: Purity of the 0.5 and 5 mg/mL concentrated formulations depends on pH at 40° C. and is highest at the lowest tested pH.

Figure 2:
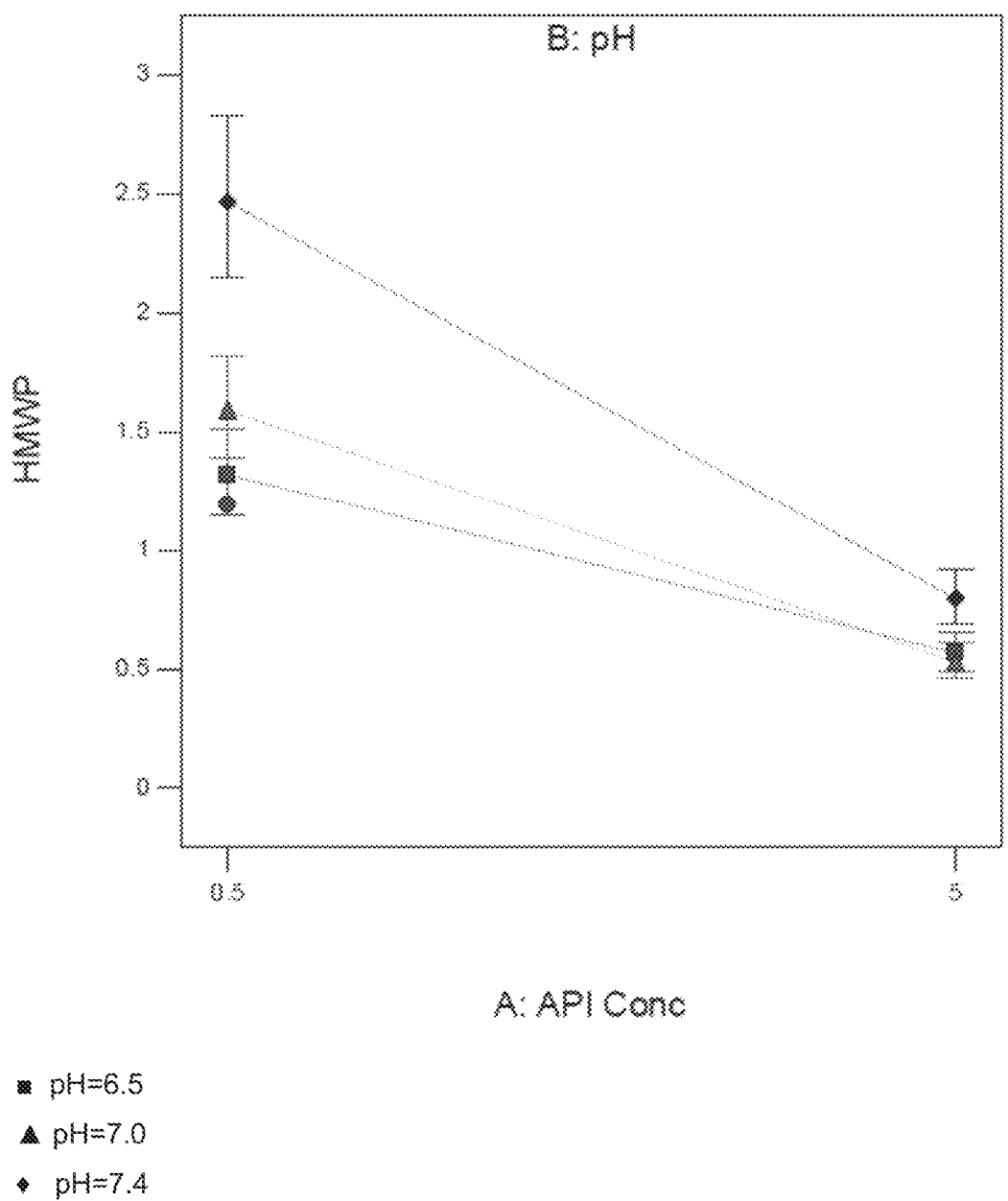

FIG. 2: HMWP content of the 0.5 and 5 mg/mL concentrated formulations depends on pH at 40° C.

Figure 3:
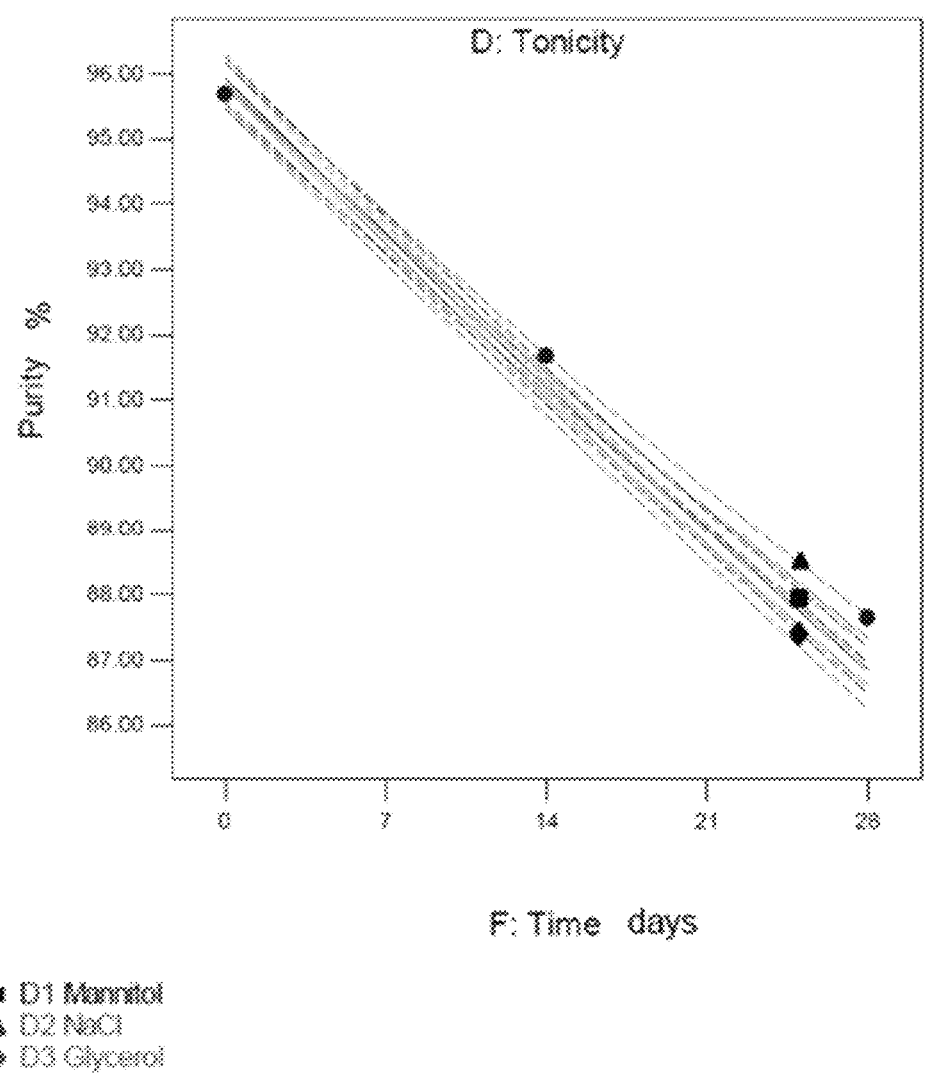

FIG. 3: Purity of the 0.5 and 5 mg/mL concentrated formulations depends on the type of tonicity adjuster and stabilizer at 40° C.

Figure 4:
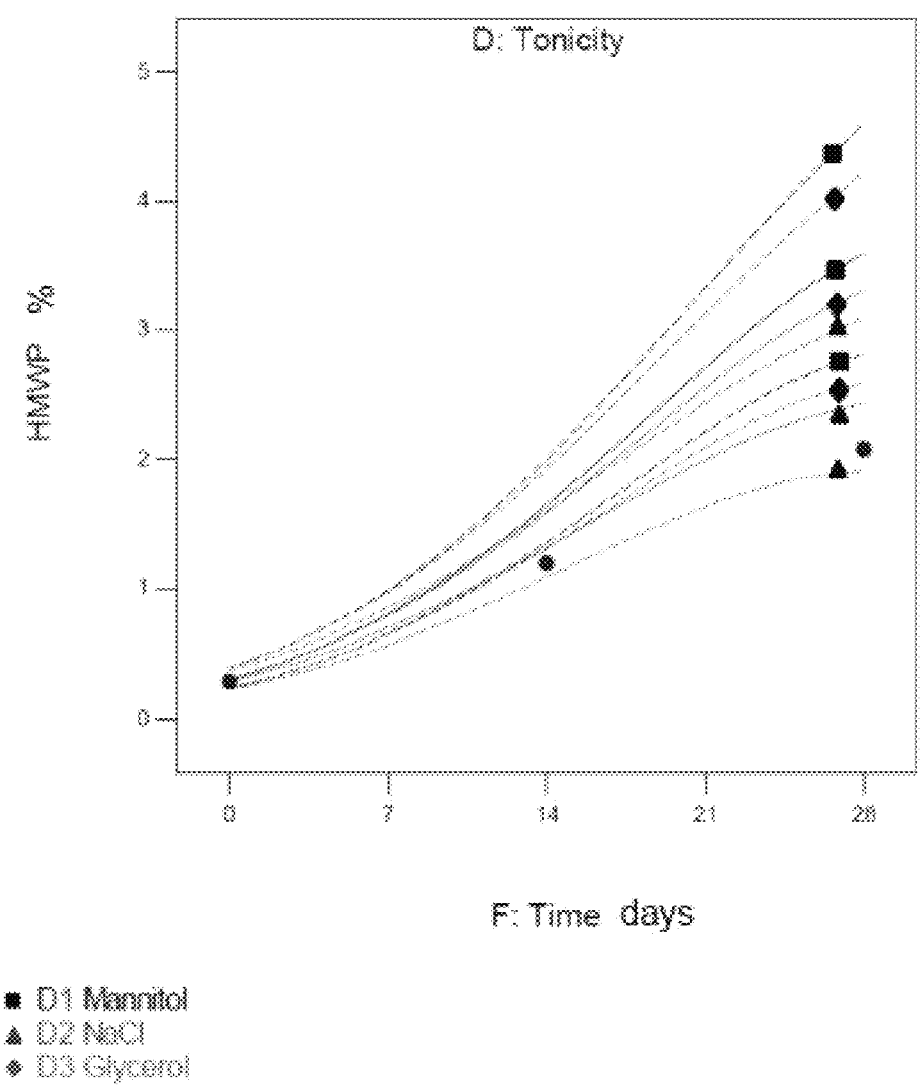

FIG. 4: HMWP content of the 0.5 and 5 mg/mL concentrated formulations depends on the type of tonicity adjuster and stabilizer at 40° C.

Figure 5:
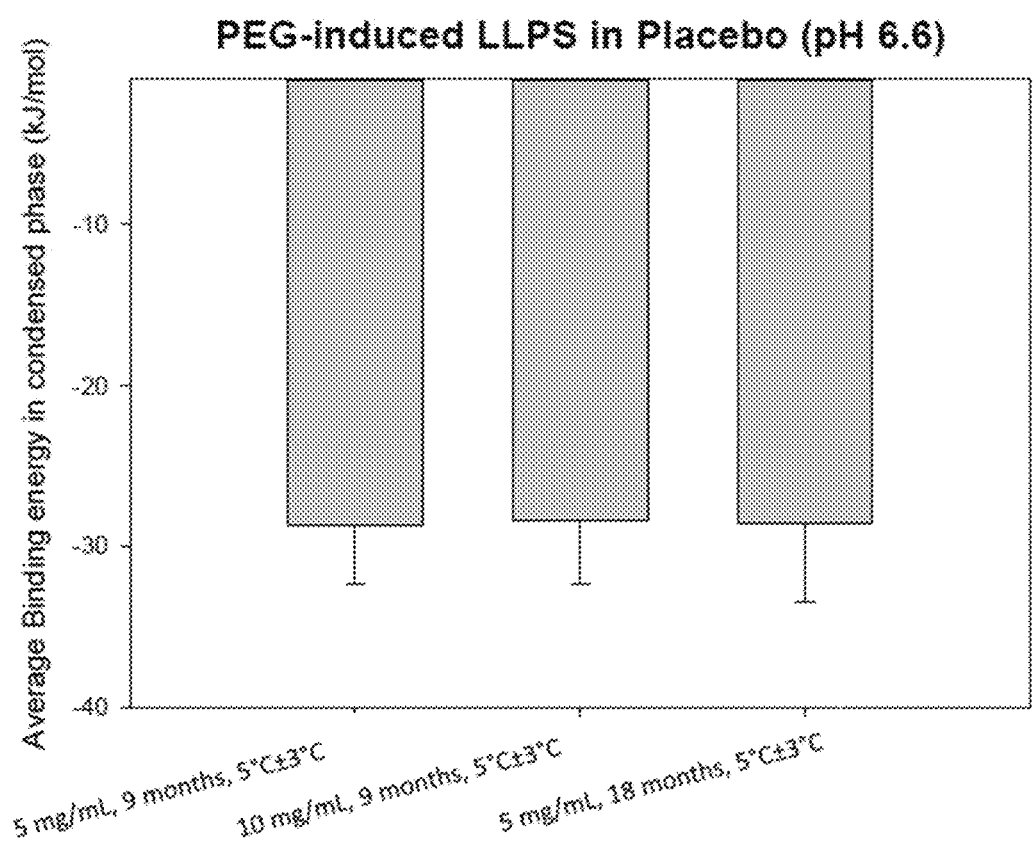

FIG. 5: Binding energy of stability samples of the formulations containing sodium chloride.

Figure 6A:
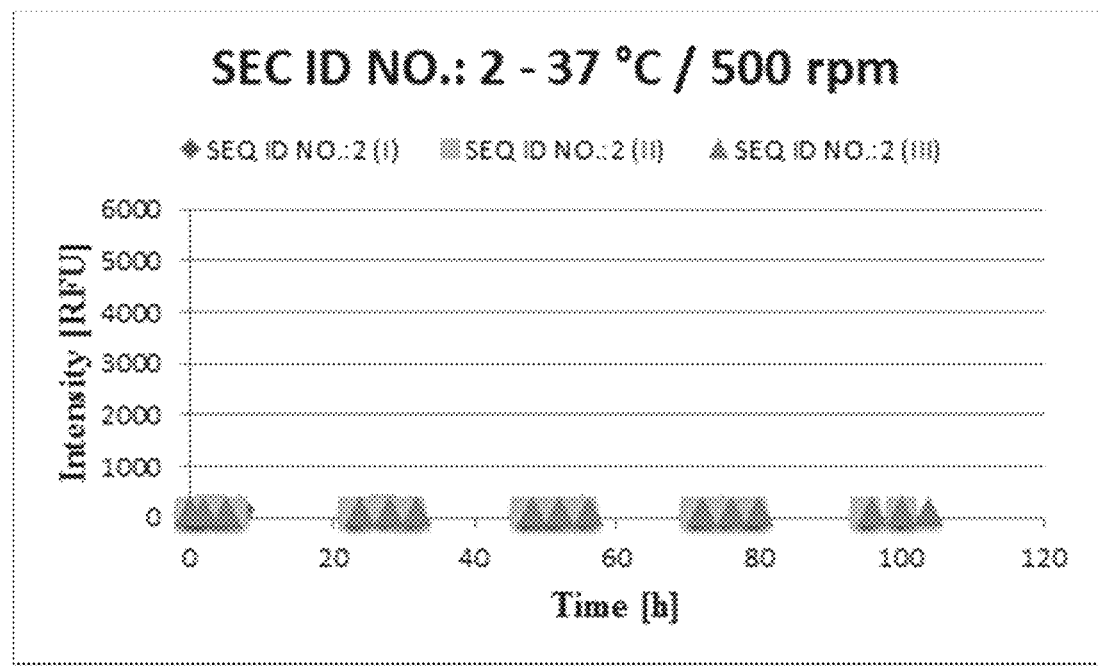
Figure 6B:
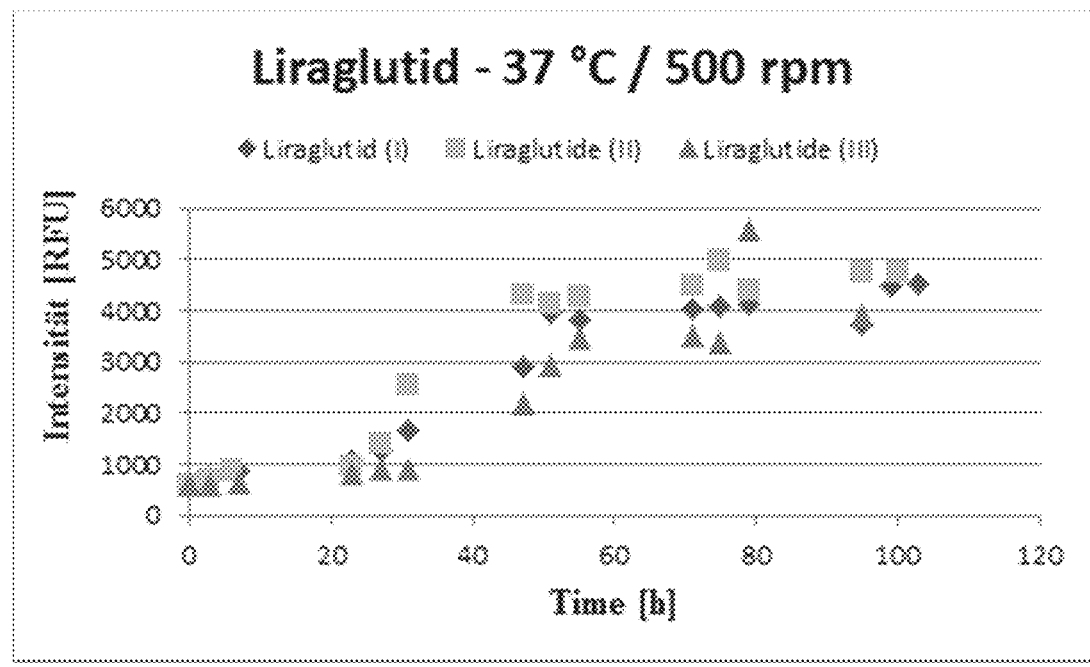
Figure 6C:
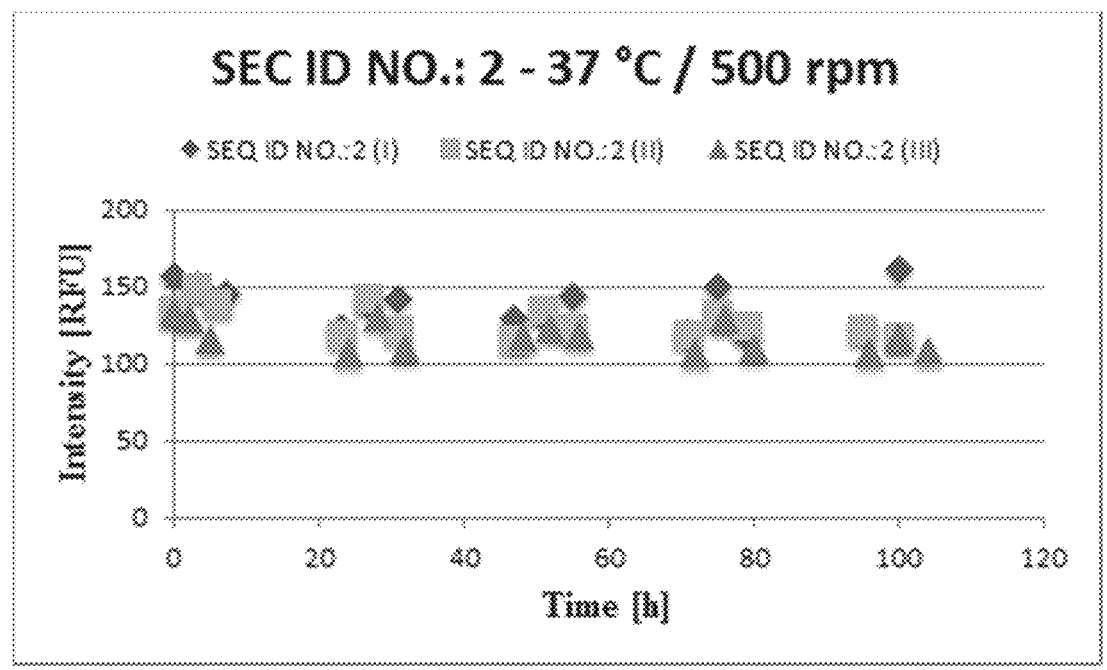

FIGS. 6A-6C: Comparative ThT test of Liraglutide and SEQ ID NO.: 2. FIG. 6A: SEQ ID NO.: 2, +37° C., 500 rpm; y-axis range 0-6000 RFU (relative fluorescence units); FIG. 6B: Liraglutide, +37° C., 500 rpm; y-axis range 0-6000 RFU; FIG. 6C: SEQ ID NO.: 2, +37° C., 500 rpm; y-axis range 0-200 RFU.

Figure 7:
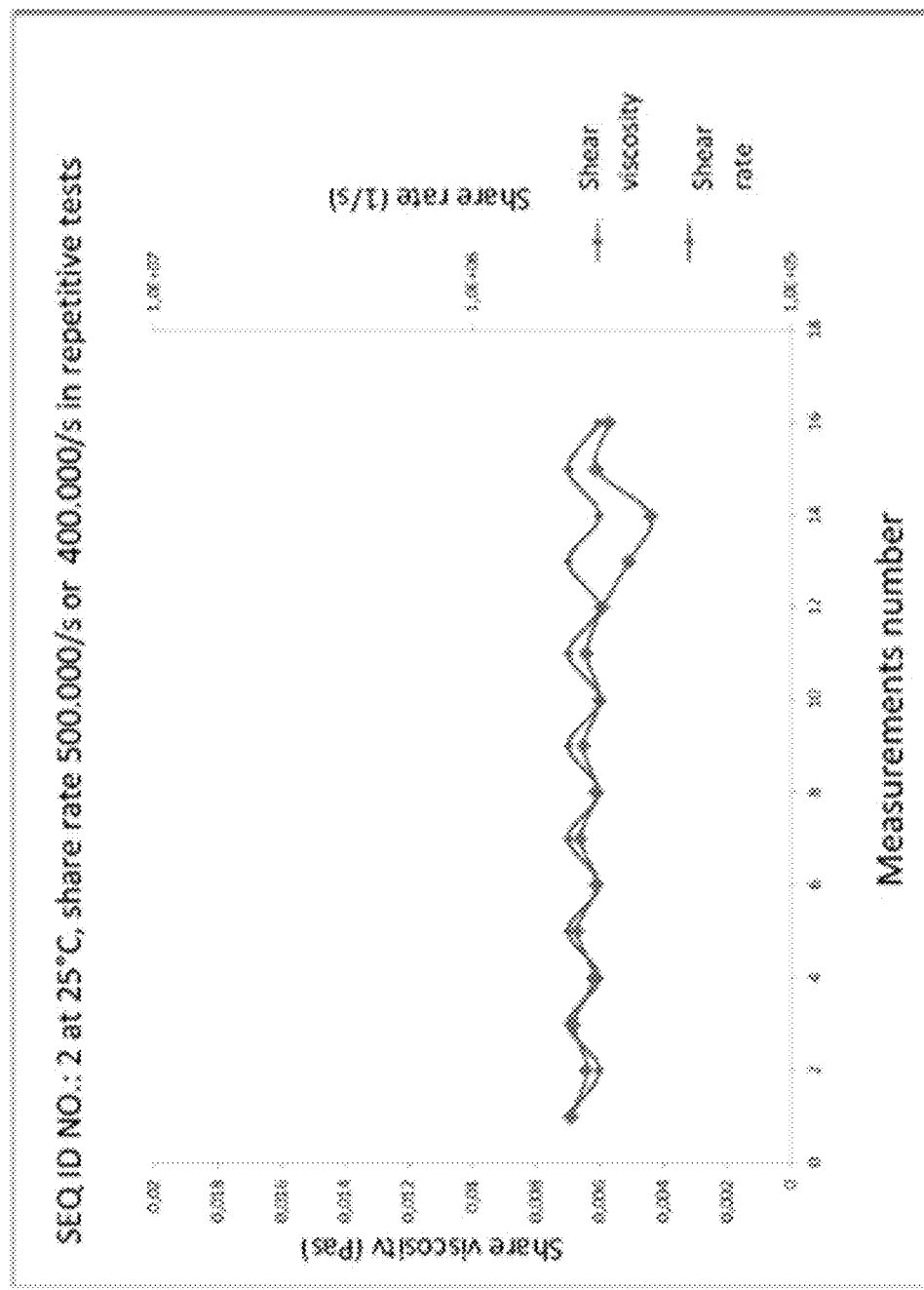

FIG. 7: Rheology evaluation of the formulation with a capillary rheometer.

EXAMPLES

Abbreviations employed are as follows:
ACN: acetonitrile
API: active pharmaceutical ingredient
DLS: dynamic light scattering
FTIR: Fourier transform infrared spectroscopy
GCG: glucagon
GLP-1: glucagon-like peptide 1
HMWP: high molecular weight protein
HPLC: high pressure liquid chromatography
HPSEC: high-performance size-exclusion chromatography
LLPS: liquid liquid phase separation
PEG: polyethylene glycol
RH: relative humidity
TFA: trifluoroacetic acid
ThT: Thioflavin T

Example 1: Chemical Stability Assessment

Detection and quantification of impurities and degradation products are carried out by reverse phase liquid chromatography (HPLC) using a gradient method with UV detection. In HPLC, impurities were calculated using the peak area percent method, and API content was calculated by external standardization.

Column: stainless steel, 150 mm×4.6 mm i.d. (XSelect CSH C18, 2.5 μm, Waters).

Mobile phase: water/acetonitrile/trifluoroacetic acid.

Flow rate: 1.0 mL/min.

Temperature: +45° C.

Detection wavelength: UV at 210 nm

Test solution: 0.5 mg/mL of test sample (undiluted for 0.5 mg/formulation, diluted with acetonitrile/water for 5.0 mg/mL formulation).

The amount of high molecular weight proteins is determined using high performance size exclusion chromatography (HPSEC). In HPSEC, HMWPs were calculated using the peak area percent method.

Column: stainless steel, 300 mm×7.8 mm i.d. (Insulin HMWP Column, Waters, or equivalent).

Mobile phase: arginine buffer/acetonitrile/acetic acid.

Flow rate: 0.45 mL/min.

Temperature: room temperature

Detection wavelength: UV at 283 nm

Test solution: 0.5 mg/mL of test sample (undiluted for 0.5 mg/formulation, diluted with acetonitrile/water for 5.0 mg/mL formulation).

A study was initiated with 20 runs of a design of experiment (DoE) study to determine the optimal type of the tonicity adjuster and/or stabilizer and to verify the pH, which ensures the highest chemical stability of peptide SEQ ID NO.: 2 as the active pharmaceutical ingredient (API). The stability study was initiated at 5° C., 25° C. and at 40° C. with 2 and 4 weeks storage conditions.

In the statistical design, the effect of concentration of the API was tested at 2 levels, the effect of pH at three levels, the effect of preservatives at three levels, the effect of tonicity adjusters at three levels and the effect of additives at two levels. Table 1a below shows a summary of the controlled factors, and Table 1b shows details of the 20 runs.

The proposed design is an IV-optimal response surface design which allows studying main effects and level 2 interactions with API in a minimum of experiments. The results at the beginning and after 14 and 28 days of storage are combined for analysis to allow the estimation of linear and quadratic effect of the factor time and corresponding level 2 interactions.

The data for the different storage conditions is analyzed independently. A backward selection is performed to keep in the model only the terms that have a significant effect at 10%.

The Box-Cox method is also used to apply a data transformation if necessary. The "Box-Cox method" refers to a systematic test of possible transformations to ensure normal distribution of the data and low variability around the model (e.g. for a linear regression, all individual measurements are as close as possible to the regression line). After analysis of each parameter a desirability function, using the relative weights defined by the scientist, is performed to obtain a global optimum.

TABLE 1a

List of controlled factors

| Factor (unit) | Description | Experimental domain |
|---|---|---|
| API Concentration (Quantitative, mg/mL) | | 2 fixed levels: 0.5 mg/ml, 5 mg/ml |
| pH (Quantitative, NA) | | 3 fixed levels: 6.5, 7.0, 7.4 |
| Preservatives (Qualitative, NA) | Phenol: 6 mg/g, m-cresol: 3 mg/g | 3 modalities: m-cresol, phenol, m-cresol + phenol |
| Tonicity adjusters (Qualitative, NA) | Glycerol 85%: 5.0 mg/g, mannitol: 8.7 mg/g, NaCl: 1.7 mg/g | 3 modalities: glycerol, mannitol, NaCl |
| Solvent (Qualitative, NA) | Propylene glycol: 7.5 mg/g | 2 modalities: propylene glycol, none |

NA: not applicable

TABLE 1b

Proposed design with 20 runs

| Run | API concentration (mg/ml) | pH | Preservatives | Tonicity adjusters | Additives |
|---|---|---|---|---|---|
| 1 | 5 | 6.5 | phenol | Mannitol | None |
| 2 | 0.5 | 7.0 | m-cresol | NaCl | propylene glycol |
| 3 | 5 | 7.0 | m-cresol + phenol | Mannitol | None |
| 4 | 5 | 7.4 | phenol | NaCl | None |
| 5 | 0.5 | 6.5 | m-cresol | Glycerol | None |
| 6 | 5 | 7.4 | m-cresol + phenol | Glycerol | None |
| 7 | 0.5 | 7.4 | m-cresol + phenol | NaCl | None |
| 8 | 5 | 6.5 | m-cresol + phenol | NaCl | propylene glycol |
| 9 | 0.5 | 6.5 | m-cresol + phenol | Mannitol | propylene glycol |
| 10 | 5 | 7.4 | m-cresol | Mannitol | propylene glycol |
| 11 | 0.5 | 7.4 | phenol | Glycerol | propylene glycol |
| 12 | 5 | 7.0 | phenol | Glycerol | propylene glycol |
| 13 | 5 | 6.5 | m-cresol | Glycerol | None |
| 14 | 0.5 | 7.0 | m-cresol + phenol | Glycerol | propylene glycol |
| 15 | 0.5 | 7.0 | phenol | Mannitol | None |
| 16 | 5 | 7.0 | m-cresol | NaCl | None |
| 17 | 0.5 | 6.5 | phenol | NaCl | propylene glycol |
| 18 | 0.5 | 7.4 | m-cresol | Mannitol | propylene glycol |
| 19 | 0.5 | 7.0 | m-cresol | NaCl | propylene glycol |
| 20 | 5 | 7.0 | m-cresol + phenol | Mannitol | None |

The purity of the active ingredient (API; SEQ ID NO.:2) and the content of high molecular weight protein (HMWP) in the test formulations depend on the pH value, as can be seen in the results presented in FIGS. 1 and 2.

FIG. 1 is an interaction plot showing differences in purity between different pH values for low API concentration. The circle is the design point; X1-axis=API concentration; X2-axis=pH; actual factors: preservative=phenol; tonicity adjuster=NaCl; solvent=propylene glycol; time=14 d.

FIG. 2 is an interaction plot showing differences in HMWP depending on the pH for low API concentration. The circle is the design point; X1-axis=API concentration; X2-axis=pH; actual factors: preservative=phenol; tonicity adjuster=NaCl; solvent=propylene glycol; time=14 d.

The highest purity and the lowest content of HMWP were found at pH 6.5/6.6.

The purity and high molecular weight protein (HMWP) content of the test formulations further depend on the type of the tonicity adjuster and stabilizer as shown in FIGS. 3 and 4. Formulations manufactured with NaCl as tonicity adjuster have significantly higher stability, higher purity and lower HMWP formation than formulations manufactured with other type of tonicity adjusters such as mannitol and glycerol.

FIG. 3 is a main effects plot showing a smaller decrease in purity when sodium chloride is used as tonicity adjuster, as compared to mannitol and glycerol. The circles in the figure are the design points, the dashed lines the CI bands; X1-axis=time; X2-axis=tonicity; actual factors: API concentration=0.5 mg/ml; pH=6.5; preservative=phenol; solvent=propylene glycol.

FIG. 4 is an Interaction plot showing the differences between isotonizers with respect to HMWP in time. The circles in the figure are the design points, the dashed lines the CI bands; X1-axis=time; X2-axis=tonicity; actual factors: API concentration=0.5 mg/ml, pH=6.5; preservative=phenol; solvent=propylene glycol.

The highest purity and the lowest content of HMWP were found for the compositions contain NaCl as a tonicity adjuster and stabilizer.

As can be seen in FIG. 1-4, the strongest effects besides time and its interactions are API concentration, pH and tonicity.

To summarize the data represented in FIGS. 1-4, the highest purity is obtained for a high API concentration, low pH and NaCl as a tonicity adjuster.

Example 2: Physical Stability Evaluation a) Colloidal Stability

The purpose of the study was to evaluate the colloidal stability of the formulation that contains an ionic tonicity adjuster and stabilizer with Liquid Liquid Phase Separation (LLPS) method. Colloidal stability, which is a measure of interaction of colloidal molecules in the solution, can be expressed in terms of binding energy. Liquid-liquid phase separation is caused by net attraction between the colloidal molecules (e.g. proteins, peptides), thus measures the interaction of molecules in the solution in terms of binding energy. Polyethylene glycol (PEG) induced liquid-liquid phase separation is a rapid quantitative way of estimating net intermolecular attractive interaction of the colloidal (antibodies or peptide) solution and can be used to get information on the propensity of a candidate or formulations to form aggregates.

Binding energy is indicative of colloidal stability was calculated using the equation of Wang et al. (Mol. Pharm. 11(5), 1391-1402, 2014):

$$\ln\left(\frac{v_0 N_A}{M_1} C_I^1\right) = -\frac{\varepsilon_B}{kT} - \Delta v \frac{\Pi_2}{kT}$$

with
$N_A$=Avogadro's number
$M_1$=molecular weight of the molecule
$C^1_I$=molecule mass concentration in the supernatant
k=Boltzmann constant
T=absolute temperature
$v_0$=volume per molecule in the condensed phase
$\Pi$=osmotic pressure of PEG
$\Delta v$=depletion zone per protein in the liquid condensed phase To evaluate the colloidal stability of a solution for injection comprising peptide SEQ ID NO.: 2 as active ingredient at 5.0 mg/mL and 10.0 mg/mL, a PEG induced LLPS study was conducted on nine and eighteen months stability samples.

Preparation of Polyethylene glycol solution was carried out as follows. 40% (w/v) solution of Polyethylene glycol was dissolved in Placebo solution. The pH of solution was adjusted to 6.6 using 1N sodium hydroxide. PEG solution was stored at +2° C.-+8° C. for 3 days and pH was again checked for pH drift.

A mixture of an API (SEQ ID NO.: 2) containing sample (5.0 mg/ml or 10.0 mg/ml API, sodium phosphate buffer, m-cresol, sodium chloride, pH for details see Table 2 below) and PEG solution was incubated at +5° C. for 2 days. After incubation sample-PEG mixture was centrifuged for two minutes at 16900 G at +5° C. After centrifugation, supernatants were transferred for RP-HPLC analysis for equilibrium peptide concentration measurements, the same HPLC method was applied as it is explained under Example 1.

Binding energy of all three stability samples was negative, which suggests that inter-peptide interactions between the peptide molecules are highly repulsive (FIG. 5). Binding energy of the peptide at 5 mg/mL, stability at 5° C. for 9 and 18 months and binding energy of the peptide at 10 mg/mL, stability at 5° C. for 9 months was not significantly different. Binding energy data of the peptide at 5 mg/mL concentrated formulation incubated at 5° C. for 9 and 18 months suggests that the colloidal stability of the peptide in 5 mg/mL concentration does not change upon extended incubation at 5° C. Comparison of 5 mg/mL and 10 mg/mL samples incubated at 5° C. for 9 months suggests that the peptide at both concentrations is equally stable.

b) Small Angle X-Ray Scattering (SAXS)

Small angle X-ray scattering (SAXS) reveals solution structures of biological macromolecules and synthetic nanoparticles at 1-2 nm resolution.

SAXS measurements were performed at a synchrotron light source (DESY Hamburg). The scattering data from all samples were collected loading 20 microliters of solutions into the capillary and flowing the whole volume across the X-ray beam. Per each sample 20 frames of 0.045 s exposure were collected and, after a statistical consistency check, averaged. The corresponding signals collected for the placebo was then subtracted. Each sample measurement was repeated at least twice to ensure reproducibility.

The best fit between the experimentally observed small angle X-ray scattering curve and the calculated one is obtained using a model in which SEQ ID NO.: 2 is all hexameric in the formulations. All hexameric means that all peptide molecules are arranged in physical oligomers containing 6 molecules of SEQ ID NO.: 2.

c) Dynamic Light Scattering (DLS)

The light-scattering intensity of particles is proportional to the diameter and therefore extremely sensitive to aggregation. For the analysis of incretin peptides, DLS is used as a standard method to measure aggregation. If high molecular weight particles are detected, this may be an artifact of the fact that the buffer has not been sufficiently filtered. On the other hand, if no high molecular weight intensity is measured; this means that no aggregates were present in the sample.

DLS experiments were performed with a Malvern Zetasizer Nano ZS. The formulation was pipetted into the measuring cell, the temperature was equilibrated to +25° C. and measured in NIBS (Non-Invasive Back-Scatter) mode.

Dynamic light scattering was performed with a composition of the invention (0.5 mg/ml and 5.0 mg/ml, respectively, phosphate buffer, NaCl and m-cresol, pH of about 6.6; for details see Table 2 below) to monitor the hydrodynamic diameter. For both API concentrations, a hydrodynamic diameter of about 6 nanometers was found. The value of 6 nm indicates that the API is present in the form of a hexamer (see above). These results further support the absence of undesired larger aggregates, for which larger hydrodynamic diameters (such as 100 nm) would have been measured. These results are in line with the SAXS results.

Example 3: Fibrillation Tendency

Investigations were carried out to determine fibrillation tendencies under stress conditions using a ThT assay. ThT is a dye that, after binding to beta-sheet-rich structures displays an enhanced fluorescence and a characteristic red shift of the emission spectrum. Amyloid-like structures show a beta-sheet rich structure. Fibrillation of peptide solutions is induced by thermic and mechanical stress. Samples are stressed under defined conditions using Fluoroskan Ascent FL.

For the tests in Fluoroskan Ascent FL 200 µL sample were placed into 96 well microtiterplate PS, flat bottom, Greiner Fluotrac No. 655076. Plates were sealed with Scotch Tape (Quiagen). Samples were stressed by continuous cycles of 10 s shaking at 960 rpm and 50 s rest period at +37° C. The kinetic was monitored by measuring fluorescence intensity every 20 minutes.

Solutions were transferred in 2 mL Eppendorf vials and 20 µL of a 10.1 mM ThT solution in $H_2O$ were added to 2 mL of peptide solution to receive a final concentration of 100 µM ThT. For each sample eight replicates were tested.

It was found that the peptide of SEQ ID NO.: 2 (at a concentration of 1 mg/ml in PBS) is more resistant to mechanical and thermal stress than Liraglutide (SEQ ID NO.: 1; 1 mg/ml in PBS), see FIGS. 6A-6C. The figure illustrates that the peptide of SEQ ID NO.:2, in contrast to Liraglutide, shows negligible fibrillation even after 100 h incubation at +37° C. and 500 rpm. In a further experiment, no fibrillation was observed after 100 hours at 37° C. shaking (500 rpm) in a solution containing 5 mg/mL SEQ ID NO.:2, phosphate buffer, NaCl and m-cresol, pH≈6.6, see Table 2 below).

Example 4: Chemical and Biophysical Evaluation

The purpose of the study was to evaluate the chemical and biophysical stability of formulations containing SEQ ID NO.: 2 with different peptide and natural salt ratios, which are 0.08 (0.5 mg: 6.30 mg) for the 0.5 mg/mL concentrated formulation, 0.8 (5 mg: 6.30 mg) for the 5.0 mg/mL concentrated formulation and 0.24 (1.5 mg: 6.30 mg) for the 1.5 mg/mL concentrated formulation.

The following composition was tested:

TABLE 2 tested composition

| Substance | Specification according to pharmacopeia | Amount per unit |
|---|---|---|
| Peptide of SEQ ID NO.: 2 | Sanofi-Aventis | 0.50 mg (Batch A) or 5.0 mg (Batch B) or 1.5 mg (Batch C) |
| Sodium dihydrogen phosphate dihydrate | Ph. Eur./USP | 3.03 mg |
| Di-sodium hydrogen phosphate dodecahydrate | Ph. Eur./USP | 3.77 mg |
| m-cresol | Ph. Eur./USP | 3.15 mg |
| Sodium chloride | Ph. Eur./USP | 6.30 mg |
| 0.1 N Hydrochloric acid | Ph. Eur./USP | ad pH 6.6 |
| 0.1 N NaOH solution | Ph. Eur./USP | ad pH 6.6 |
| Water for injection (WfI) | Ph. Eur./USP | ad 1.0 ml |

The formulations are stored in units which are intended for clinical studies and for sales and distribution.

Storage times, storage conditions, time points are summarized in the following table.

TABLE 3 summary conditions

| Condition | Test interval (months) | | | |
|---|---|---|---|---|
| | 0 | 1 | 3 | 6 |
| Long-term storage +5 ± 3° C. | x | x | x | x |
| Accelerated conditions (temperature, humidity) +25 ± 2° C./60 ± 5% RH | x | x | x | x |
| +37 ± 2° C./75 ± 5% RH | x | x | — | — |

The formulations storage orientation was inverted. RH means relative humidity. Time point 0 is the start of storage. The measurements at time point 0 are used as a reference for all conditions tested.

The physical and chemical stability of the stored formulations is determined with the help of the following tests:
- Dynamic light scattering (DLS) method was applied to access the subvisible particle size distribution
- Fourier transform infrared spectroscopy (FTIR) to analyze the ratio of alpha and beta sheets
- Chemical stability (purity and impurities), determined by HPLC
- Proteins of high molecular weight, determined by HPSEC All values were determined by HPLC with the so-called 100% method. Here, in particular, it involves reversed-phase HPLC (C 18 column), in which a gradient method was used for the mobile phase:

a) 0.1% TFA, 15% ACN and b) 0.1% TFA, 75% ACN. Detection at 210 nm (UV).

The high-molecular-weight proteins (HMWP) were detected by HPSEC, described in European Pharmacopeia 6.0 for injectable insulin preparations.

The percentage values are the content values (percentage values of impurities) of total impurities, and of high-molecular-weight proteins (HMWP).

Results

The formulations were studied separately for parallel batches A (0.5 mg/ml API), B (5.0 mg/ml API) and C (1.5 mg/ml) with regard to the following parameters:

Biophysical stability with the evaluation of DLS and FTIR results. Physical instability was not observed even for a high sodium chloride containing formulation (0.5 mg/mL peptide with 6.3 mg/mL sodium chloride concentration). The DLS and FTIR data were stable during the stability study and an increase in the beta sheet was not analysed.

Total impurities. An increase in the sum of impurities/degradation products was observed. This increase is not due to an increase of one single impurity, but a slight increase of about 0.1 to 0.2% is observed for various impurities. Stability results support the minimum 24 months shelf life of the drug product independently from the concentration of the active pharmaceutical ingredient within the formulation.

High molecular weight proteins (HMWPs). There is only a slight increase in high molecular weight proteins observed at 5° C. and 25° C. At 37° C. after 1 month storage the increase is between 0.3 and 0.7% and results are within the specification 2.0%.

The data are summarized in the following table:

TABLE 4

Summary Results

Batch A: 0.5 mg/mL

| +5° C. | t₀ | 1 Mon. | 3 Mon. | 6 Mon. | 9 Mon. | 12 Mon. | 18 Mon. | 24 Mon. |
|---|---|---|---|---|---|---|---|---|
| SEQ ID NO.: 2 assay in mg/mL | 0.50 | 0.50 | 0.49 | 0.50 | 0.50 | 0.51 | 0.51 | 0.50 |
| Total impurities in % | 3.1 | 3.1 | 3.7 | 3.9 | 4.3 | 4.7 | 4.9 | 6.0 |
| Proteins of high molecular weight in % | 0.4 | 0.5 | 0.5 | 0.5 | 0.7 | 0.9 | 1.0 | 1.0 |
| FTIR: alpha/beta sheets in % | 50.3/16.7 | — | — | 47.5/17.5 | — | 53.2/22.6 | 48.1/11.7 | 50.2/12.8 |
| DLS in nm | — | — | — | — | — | — | — | — |

| +25° C. | t₀ | 1 Mon. | 3 Mon. | 6 Mon. |
|---|---|---|---|---|
| Activity assay in mg/mL | 0.50 | 0.49 | 0.47 | 0.46 |
| Total impurities in % | 3.1 | 4.1 | 7.1 | 10.0 |
| Proteins of high molecular weight in % | 0.4 | 0.7 | 0.9 | 1.5 |
| FTIR: alpha/beta sheets in % | 50.3/16.7 | — | — | 46.7/20.8 |
| DLS in nm | — | — | — | — |

| +37° C. | t₀ | 1 Mon. | 3 Mon. | 6 Mon. |
|---|---|---|---|---|
| SEQ ID NO.: 2 assay in mg/mL | 0.50 | 0.46 | — | — |
| Total impurities in % | 3.1 | 8.1 | — | — |
| Proteins of high molecular weight in % | 0.4 | 1.1 | — | — |
| FTIR: alpha/beta sheets in % | 50.3/16.7 | — | — | — |
| DLS in nm | — | — | — | — |

Batch B: 5.0 mg/mL

| +5° C. | t₀ | 1 Mon. | 3 Mon. | 6 Mon. | 9 Mon. | 12 Mon. | 18 Mon. | 24 Mon. |
|---|---|---|---|---|---|---|---|---|
| SEQ ID NO.: 2 assay in mg/mL | 5.13 | 5.20 | 5.08 | 4.96 | 5.12 | 5.26 | 5.25 | 5.18 |
| Total impurities in % | 3.1 | 3.2 | 3.9 | 3.8 | 4.2 | 4.7 | 4.9 | 6.0 |
| Proteins of high molecular weight in % | 0.4 | 0.3 | 0.3 | 0.4 | 0.4 | 0.6 | 0.6 | 0.7 |
| FTIR: alpha/beta sheets in % | 46.9/13.9 | — | — | 48.0/15.5 | — | 52.0/12.3 | 47.6/12.8 | 49.5/13.9 |
| DLS in nm | 5.93 | — | — | 6.15 | — | — | 6.02 | 5.60 |

| +25° C. | t₀ | 1 Mon. | 3 Mon. | 6 Mon. |
|---|---|---|---|---|
| Activity assay in mg/mL | 5.13 | 5.06 | 4.78 | 4.56 |
| Total impurities in % | 3.1 | 4.3 | 7.5 | 9.9 |

TABLE 4-continued

| Summary Results | | | | |
|---|---|---|---|---|
| Proteins of high molecular weight in % | 0.4 | 0.4 | 0.5 | 0.7 |
| FTIR: alpha/beta sheets in % | 46.9/ 13.9 | — | — | 48.1/ 16.1 |
| DLS in nm | 5.93 | — | — | 6.13 |

| +37° C. | $t_0$ | 1 Mon. | 3 Mon. | 6 Mon. |
|---|---|---|---|---|
| SEQ ID NO.: 2 assay in mg/mL | 5.13 | 4.79 | — | — |
| Total impurities in % | 3.1 | 8.8 | — | — |
| Proteins of high molecular weight in % | 0.4 | 0.7 | — | — |
| FTIR: alpha/beta sheets in % | 46.9/ 13.9 | — | — | — |
| DLS in nm | 5.93— | — | — | |

| Batch C: 1.5 mg/mL | | | | | | |
|---|---|---|---|---|---|---|
| +5° C. | $t_0$ | 3 Mon. | 6 Mon. | 12 Mon. | 18 Mon. | 24 Mon. |
| SEQ ID NO.: 2 assay in mg/mL | 1.47 | 1.46 | 1.39 | 1.43 | 1.43 | 1.39 |
| Total impurities in % | 3.9 | 4.4 | 5.1 | 5.3 | 6.1 | 6.0 |
| Proteins of high molecular weight in % | 0.6 | 0.6 | 0.7 | 0.7 | 0.7 | 0.8 |

| +25° C. | $t_0$ | 3 Mon. | 6 Mon. |
|---|---|---|---|
| Activity assay in mg/mL | 1.47 | 1.38 | 1.26 |
| Total impurities in % | 3.9 | 8.0 | 12.3 |
| Proteins of high molecular weight in % | 0.6 | 1.0 | 1.4 |

Conclusion

The results of the accelerated and long term stability study verified the observations of the initial short term experiments (storage for 2 and 4 weeks). Sodium chloride ensured the suitable chemical and biophysical stability of the active pharmaceutical ingredient in 0.08, 0.24 and 0.8 peptide to neutral salt ratio.

Example 5: Ratio of Alpha and Beta Sheets

FTIR spectroscopy is a suitable method for the determination of a protein's secondary structure. The vibration giving the most pronounced signal in FTIR spectroscopy is the C=O stretching vibration of amide groups resulting in a signal in the so-called amide I-region (1700-1600 cm$^{-1}$). This vibration is sensitive to the hydrogen-bonding pattern, dipole-dipole interactions and the geometry of the polypeptide backbone. The signals obtained in this IR-region give typical bands for the different secondary structural elements of a protein. For most proteins, different secondary structural elements influence the IR-spectrum in the amide I-region.

As a consequence, the individual component bands that represent the different structural elements, such as α-helices, β-sheets, turns and irregular structures are often not resolved and difficult to identify in the broad amide I-band contours of the experimentally obtained spectra. The Opus software includes a chemometric method analysing certain regions of the amide I and amide II bands from a library of 43 proteins of known α-helix and β-sheet content. The proteins used for the calibration of the method covered a region of 0 to 75% for α-helix content and 0 to 48% for β-sheet content. The average error in predicted α-helix for the calibration proteins was 5.5%, the error in β-sheet content 4.4%, reasonable numbers for an empirical method. However, it should be kept in mind that the results for some proteins deviate far more (up to 15%) from their true values. The absolute values for protein conformation determined by the chemometric method can therefore be systematically biased, however, the repeatability of results for samples of the same protein is usually in the range of +/−2%.

Investigations were carried out to determine the ratio of alpha and beta sheets at 5.0 mg/ml and 75 mg/mL concentration, respectively, of the biopharmaceutical protein (SEQ ID NO.: 2). The tested formulation contained a phosphate buffer, m-cresol and sodium chloride (as detailed in Table 2 above).

Samples were investigated using a Bruker Tensor 27 Fourier-transform infrared (FTIR) spectrometer equipped with an AquaSpec sampling cuvette with an optical path length of 7 μm ("Confocheck" setup). Spectrometer control and data evaluation was done by the Opus software package, version 6.5. Measurements were performed as described below according to the manufacturer's instructions:

Daily system check by the automated "Performance Qualification" tool of the Opus software.

Flushing of the AquaSpec cell with water until a clean background line is achieved. In case residual peaks cannot be eliminated by purging with water alone, a 5% Hellmanex solution is used.

Two samples are subsequently measured, first the placebo (buffer) solution followed by the protein formulation. About 50 µL are injected into the cell by means of a Hamilton syringe. The difference of the two spectra is automatically generated and represents the spectrum of the pure protein. The procedure was repeated for each formulation in order to obtain two data sets for duplicate analysis.

After normalization, the spectra are evaluated by the Quant2 module of the Opus software.

The measured values of alpha and beta sheets were 48.9 and 13.1%, which are in the trend of previous FTIR results of formulations containing 0.5 and 5.0 mg/mL active pharmaceutical ingredient.

Example 6: Effect of Surfactants

Formulations were manufactured to evaluate the effect of surfactants such as Polysorbate 20, Polysorbate 80 and Poloxamer 188 on the biophysical stability of the active pharmaceutical ingredient in a solution formulation. Formulations were manufactured at pH=7.4 with 5.0 mg/mL active pharmaceutical ingredient concentration. Interestingly, the particle size measured with the DLS method (general method description: see above) increased for the formulations containing especially Polysorbates up to 7.8 nm, which phenomena was explained as a micelle formation.

Example 7: Adsorption to Surfaces

Investigations were carried out to study the adsorption phenomena of the active pharmaceutical ingredient to glass and plastic surfaces of the primary containers in 0.05 mg/mL peptide concentration with a formulation containing a neutral salt such as sodium chloride. Dilution of the 0.5 mg/mL concentrated formulation described above (see Table 2) was done with 0.9% NaCl containing solution to reach the 0.05 mg/mL concentration. The diluted formulation was stored in glass and in plastic containers. As explained above, the formulation contains a buffer and a microbiological preservative. Assay results showed the best recovery as compared to the assay results in 10 times higher (0.5 mg/mL) concentration, close to 100%, of the theoretical assay from glass containers.

Detection of the assay values at the end of the adsorption time were carried out by reverse phase liquid chromatography (HPLC) using a gradient method with UV detection (see above).

Example 8: Rheological Properties of the Formulations

Investigations were carried out to evaluate the fluid property of the formulation to determine whether it is a Newtonian fluid or not. To this end, a composition as described above in Table 2 containing 5.0 mg/ml SEQ ID NO.: 2 was added to a rheometer and subjected to measurement. The experiments were performed with a MCR rotation rheometer (Anton Paar) and with capillary rheometer Kinexus (Malvern). No significant changes were observed in shear stress or viscosity at shear rates>1/s* (Newtonian fluid). High shear rates have no influence on the shear viscosity of the formulation (see also FIG. 7).

The invention is further characterized by the following items:

Item 1. A liquid composition comprising a peptide of SEQ ID NO.: 2 and/or a pharmaceutically acceptable salt thereof as an active pharmaceutical ingredient, sodium chloride, and a liquid carrier.

Item 2. The composition of item 1, wherein the active pharmaceutical ingredient is present in an amount of 1 µg/ml to 75 mg/ml.

Item 3. The composition of item 1 or 2, wherein the active pharmaceutical ingredient is present in an amount of 1 µg/ml to 10 mg/ml.

Item 4. The composition of any one of items 1-3, wherein the active pharmaceutical ingredient is present in an amount of 0.5 mg/ml to 5 mg/ml.

Item 5. The composition of any one of items 1-4, wherein sodium chloride is present in an amount of 0.5 mg/ml to 9 mg/ml.

Item 6. The composition of any one of items 1-5, wherein sodium chloride is present in an amount of 5 mg/ml to 9 mg/ml.

Item 7. The composition of any one of items 1-6, wherein the composition further comprises a pharmaceutically acceptable preservative.

Item 8. The composition of item 7, wherein the pharmaceutically acceptable preservative is selected from phenol and m-cresol.

Item 9. The composition of item 7 or 8, wherein the pharmaceutically acceptable preservative is m-cresol.

Item 10. The composition of any one of items 1-9, wherein the composition further comprises a pharmaceutically acceptable buffer.

Item 11. The composition of any one of items 1-10, wherein the pharmaceutically acceptable buffer is selected from the group consisting of a phosphate buffer, a citrate buffer, and a phosphate-citrate buffer.

Item 12. The composition of any one of items 1-11, wherein the pharmaceutically acceptable buffer is a phosphate buffer.

Item 13. The composition of item 12, wherein the phosphate buffer is a sodium phosphate buffer.

Item 14. The composition of any one of items 1-11, wherein the pharmaceutically acceptable buffer is a citrate buffer.

Item 15. The composition of item 14, wherein the citrate buffer is a sodium citrate buffer.

Item 16. The composition of any one of items 1-15, wherein the composition has a pH from 6.0 to 7.0.

Item 17. The composition of any one of items 1-16, wherein the composition has a pH from 6.2 to 6.9.

Item 18. The composition of any one of items 1-17, wherein the composition has a pH of about 6.6, particularly 6.55-6.64.

Item 19. The composition of any one of items 1-18, wherein the liquid carrier is an aqueous liquid.

Item 20. The composition of any one of items 1-19, wherein the liquid carrier is water.

Item 21. The composition of any one of items 1-20, wherein the liquid carrier is free of any organic solvent.

Item 22. The composition of any one of items 1-20, which is free of any organic solvent.

Item 23. The composition of any one of items 1-20, wherein the liquid carrier is free of glycerol.

Item 24. The composition of any one of items 1-20, which is free of glycerol.

Item 25. The composition of any one of items 1-20, 23, wherein the liquid carrier is free of propylene glycol.

Item 26. The composition of any one of items 1-20, 24, which is free of propylene glycol.

Item 27. The composition of any one of items 1-26, which exhibits biological activity of the active pharmaceutical ingredient(s) (API(s)) after storage.

Item 28. The composition of item 27, wherein the composition is stored for 1 month, 3 months, 6 months, 9 months, 12 months, 18 months or 24 months.

Item 29. The composition of item 27 or 28, wherein the composition is stored at a temperature of +5° C., +25° C., or +37° C.

Item 30. The composition of any one of items 27-29, wherein the biological activity of the API(s) after storage for at least one month at a temperature of +5° C. or +25° C., is at least 80%, at least 90%, at least 95% or at least 98% of the activity at the start of storage.

Item 31. The composition of any one of items 27-30, wherein the biological activity of the API(s) after storage for twelve months or twenty-four months at a temperature of +5° C., is at least 80% of the activity at the start of storage.

Item 32. The composition of any one of items 27-30, wherein the biological activity of the API(s) after storage for one month or three months or six months at a temperature of +25° C., is at least 80% of the activity at the start of storage.

Item 33. The composition of any one of items 27-31, wherein the biological activity of the API(s) after storage for twenty-four months at a temperature of +5° C. is at least 90%, at least 95% or at least 98% of the activity at the start of storage.

Item 34. The composition of any one of items 1-33, which exhibits chemical integrity of the API(s) after storage.

Item 35. The composition of item 34, wherein at least 80%, at least 90%, at least 95% or at least 98% of the API(s) are present in a substantially chemically unchanged form after storage.

Item 36. The composition of item 34 or 35, wherein the composition is stored for 1 month, 3 months, 6 months, 9 months, 12 months, 18 months or 24 months.

Item 37. The composition of any one of items 34-36, wherein the composition is stored at a temperature of +5° C., +25° C., or +37° C.

Item 38. The composition of any one of items 34-37, wherein at least 80%, at least 90%, at least 95% or at least 98% of the API(s) are present in a substantially chemically unchanged form after storage for 18 months at +5° C.

Item 39. The composition of any one of items 34-37, wherein at least 80%, at least 90%, at least 95% or at least 98% of the API(s) are present in a substantially chemically unchanged form after storage for 6 months at +25° C.

Item 40. The composition of any one of items 34-37, wherein at least 80%, at least 90%, at least 95% or at least 98% of the API(s) are present in a substantially chemically unchanged form after storage for 1 month at +37° C.

Item 41. The composition of any one of items 34-37, wherein the composition is defined as exhibiting chemical integrity if the proportion of proteins of high molecular weight (HMWP) with respect to the entire mass of the peptide of SEQ ID NO.: 2 present in the composition after storage is below 2 wt-%.

Item 42. The composition of item 41, wherein the proportion of proteins of high molecular weight (HMWP) with respect to the entire mass of the peptide of SEQ ID NO.: 2 present in the composition after storage is below 2 wt-% after storage for one month, 6 months, 12 months or 18 months at +5° C.

Item 43. The composition of item 41, wherein the proportion of proteins of high molecular weight (HMWP) with respect to the entire mass of the peptide of SEQ ID NO.: 2 present in the composition after storage is below 2 wt-% after storage for one month, 6 months, 12 months or 18 months at +25° C.

Item 44. The composition of item 41, wherein the proportion of proteins of high molecular weight (HMWP) with respect to the entire mass of the peptide of SEQ ID NO.: 2 present in the composition after storage is below 2 wt-% after storage for one month, 6 months, 12 months or 18 months at +37° C.

Item 45. The composition of any one of items 41-44, wherein the proportion of proteins of high molecular weight (HMWP) with respect to the entire mass of the peptide of SEQ ID NO.: 2 present in the composition after storage is below 2 wt-% after storage for 18 months at +5° C., 6 months at +25° C. and/or one month at +37° C.

Item 46. The composition of any one of items 1-45, which exhibits physical integrity of the API(s) after storage.

Item 47. The composition of item 46, wherein at least 80%, at least 90%, at least 95%, or at least 98% of the API(s) are present in a substantially physically unchanged form, compared with the start of storage.

Item 48. The composition of item 46 or 47, wherein the composition is stored for 1 month, 3 months, 6 months, 9 months, 12 months, 18 months or 24 months.

Item 49. The composition of any one of items 46-48, wherein the composition is stored at a temperature of +5° C., +25° C., or +37° C.

Item 50. The composition of any one of items 46-49, wherein at least 80%, at least 90%, at least 95% or at least 98% of the API(s) are present in a substantially chemically unchanged form after storage for 18 months at +5° C.

Item 51. The composition of any one of items 46-49, wherein at least 80%, at least 90%, at least 95% or at least 98% of the API(s) are present in a substantially chemically unchanged form after storage for 6 months at +25° C.

Item 52. The composition of any one of items 46-49, wherein at least 80%, at least 90%, at least 95% or at least 98% of the API(s) are present in a substantially chemically unchanged form after storage for 1 month at +37° C.

Item 53. The composition of any one of items 46-52, which is free of aggregates, particularly covalent aggregates.

Item 54. The composition of any one of items 46-53, wherein the composition is defined as exhibiting physical integrity if it is free of covalent aggregates as determined by Dynamic Light Scattering (DLS).

Item 55. The composition of any one of items 27-54, wherein the peptide of SEQ ID NO.: 2 is the sole active pharmaceutical ingredient (API).

Item 56. The composition of any one of items 1-55, which is free of surfactants.

Item 57. The composition of any one of items 1-55, which is free of polyhydric alcohols or esters or ethers thereof, particularly free of fatty acid esters and ethers of glycerol and sorbitol.

Item 58. The composition of any one of items 1-57, which is free of polyols, particularly polyols selected from the group consisting of polypropylene glycols, polyethylene glycols, polysorbates, poloxamers, Pluronics, and Tetronics.

Item 59. The composition of any one of items 1-58, which is free of polysorbates.

Item 60. The composition of any one of items 1-59, which is free of poloxamers.

Item 61. The composition of any one of items 1-58, which is free of polysorbates and poloxamers.

Item 62. The composition of any one of items 1-61, which is free of tonicity adjusters different from sodium chloride.

Item 63. The composition of any one of items 1-61, which is free of glycerol, dextrose, lactose, sorbitol, and mannitol.

Item 64. The composition of any one of items 1-61, which is free of mannitol and propylene glycol.

Item 65. The composition of any one of items 1-64, which consists of
(a) a peptide of SEQ ID NO.: 2 and/or a pharmaceutically acceptable salt thereof,
(b) a sodium phosphate buffer of pH 6.2 to 6.9, particularly a sodium phosphate buffer of about pH 6.5 to 6.7,
(c) m-cresol,
(d) sodium chloride, and
(e) water.

Item 66. The composition of any one of items 1-65, which consists of
(a) a peptide of SEQ ID NO.: 2,
(b) a sodium phosphate buffer of pH 6.2 to 6.9, particularly a sodium phosphate buffer of about pH 6.5 to 6.7,
(c) m-cresol,
(d) sodium chloride, and
(e) water.

Item 67. The composition of any one of items 1-66, which consists of
(a) a peptide of SEQ ID NO.: 2,
(b) a sodium phosphate buffer of about pH 6.5 to 6.7,
(c) m-cresol,
(d) sodium chloride, and
(e) water.

Item 68. The composition of any one of items 1-64, which consists of
(a) a peptide of SEQ ID NO.: 2 and/or a pharmaceutically acceptable salt thereof in an amount of 0.5 mg/ml to 5 mg/ml,
(b) $NaH_2PO_4 \times 2H_2O$ in an amount of 3.03 mg/ml and $Na_2HPO_4 \times 12H_2O$ in an amount of 3.77 mg/ml,
(c) m-cresol in an amount of 3.15 mg/ml,
(d) sodium chloride in an amount of 6.30 mg/ml,
(e) optionally NaOH and/or HCl at pH 6.6, and
(f) water, particularly water for injection.

Item 69. The composition of any one of items 1-64, which consists of
(a) a peptide of SEQ ID NO.: 2 in an amount of 0.5 mg/ml to 5 mg/ml,
(b) $NaH_2PO_4 \times 2H_2O$ in an amount of 3.03 mg/ml and $Na_2HPO_4 \times 12H_2O$ in an amount of 3.77 mg/ml,
(c) m-cresol in an amount of 3.15 mg/ml,
(d) sodium chloride in an amount of 6.30 mg/ml,
(e) optionally NaOH and/or HCl at pH 6.6, and
(f) water for injection.

Item 70. The composition of any one of items 1-69 for use in medicine, particularly for use in human medicine.

Item 71. The composition of item 70 for injection.

Item 72. The composition of any one of items 1-69 for use in a method of treating diabetes mellitus, particularly for use in a method of treating type II diabetes mellitus.

Item 73. The composition of any one of items 1-69 for use in a method of treating obesity.

Item 74. The composition of any one of items 1-69 for use in a method of treating diabetes mellitus, particularly type II diabetes mellitus, and obesity.

Item 75. The composition of any one of items 1-69 for use according to item 72 or 74, wherein the diabetic patients have a HbA1c value in the range from 7% to 10%.

Item 76. The composition of any one of items 1-69 for use according to any one of items 69-74, which is for administration in patients with type II diabetes as a supplement to a diet in order to improve blood glucose control.

Item 77. A method for treating a disorder comprising administering to a patient in need thereof a therapeutically effective amount of a composition of any one of items 1-69.

Item 78. The method of item 77, wherein the patient is a human patient.

Item 79. The method of item 77 or 78, wherein said disorder is selected from the group consisting of diabetes mellitus, particularly type II diabetes mellitus, and obesity.

The invention claimed is:

1. A liquid composition comprising:
 the peptide of SEQ ID NO: 2, a pharmaceutically acceptable salt of the peptide of SEQ ID NO: 2, or a combination thereof as an active pharmaceutical ingredient;
 sodium chloride;
 a sodium phosphate buffer;
 m-cresol; and
 water
 wherein the liquid composition has a pH from 6.0 to 7.0.

2. The composition of claim 1, wherein the active pharmaceutical ingredient is present in an amount of 1 µg/ml to 75 mg/ml.

3. The composition of claim 1, wherein sodium chloride is present in an amount of 0.5 mg/ml to 9 mg/ml.

4. The composition of claim 1, wherein the composition is free of any organic solvent.

5. The composition of claim 1, wherein the composition exhibits biological activity, chemical integrity, physical integrity, or any combinations of activity and integrity thereof of the active pharmaceutical ingredient after storage.

6. The composition of claim 1, wherein the composition is free of surfactants.

7. The composition of claim 1, wherein the composition is free of tonicity adjusters different from sodium chloride.

8. The composition of claim 1, wherein the composition consists of:
 the peptide of SEQ ID NO: 2, a pharmaceutically acceptable salt of the peptide of SEQ ID NO: 2, or a combination thereof;
 a sodium phosphate buffer;
 m-cresol;
 sodium chloride; and
 water,
 wherein the liquid composition has a pH of 6.2 to 6.9.

9. The composition of claim 1, wherein the composition consists of:
 a peptide of SEQ ID NO: 2, a pharmaceutically acceptable salt of the peptide of SEQ ID NO: 2, or a combination thereof in an amount of 0.5 mg/ml to 5 mg/ml;
 $NaH_2PO_4 \times 2H_2O$ in an amount of 3.03 mg/ml and $Na_2HPO_4 \times 12H_2O$ in an amount of 3.77 mg/ml;
 m-cresol in an amount of 3.15 mg/ml;
 sodium chloride in an amount of 6.30 mg/ml;
 optionally NaOH and/or HCl; and
 water;
 wherein the liquid composition has a pH of 6.6.

10. A method of treating a subject suffering from a disease or disorder, the method comprising administering to the subject a therapeutically effective amount of the liquid composition of claim 1.

11. The method of claim 10, wherein the disease or disorder is diabetes mellitus or obesity.

12. The method of claim 11, wherein the diabetic patient has a HbA1c value in the range from about 7% to about 10%.

13. The method of claim 11, wherein the composition is for administration in a patient with type II diabetes as a supplement to a diet in order to improve blood glucose control.

14. The composition of claim 5, wherein the composition exhibits biological activity of the active pharmaceutical ingredient after storage, and wherein the storage is for about one month at a temperature of about +5° C.

15. The composition of claim 5, wherein the composition exhibits chemical integrity of the active pharmaceutical ingredient after storage, and wherein the storage is for about one month at a temperature of about +5° C.

16. The composition of claim 5, wherein the composition exhibits physical integrity of the active pharmaceutical ingredient after storage, and wherein the storage is for about one month at a temperature of about +5° C.

* * * * *

SEQUENCE LISTING

```
<160> NUMBER OF SEQ ID NOS: 2

<210> SEQ ID NO 1
<211> LENGTH: 31
<212> TYPE: PRT
<213> ORGANISM: Artificial Sequence
<220> FEATURE:
<223> OTHER INFORMATION: Liraglutide
<220> FEATURE:
<221> NAME/KEY: MOD_RES
<222> LOCATION: (20)..(20)
<223> OTHER INFORMATION: Lys is functionalized at the amino side chain
      group as Lys((S)-4-carboxy-4-hexadecanoylamino-butyryl)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 2
<211> LENGTH: 39
<212> TYPE: PRT
<213> ORGANISM: Artificial Sequence
<220> FEATURE:
<223> OTHER INFORMATION: Exendin-4 analogue
```

```
-continued

<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 2

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
            35
```